US009925033B2

(12) United States Patent
Cartledge et al.

(10) Patent No.: US 9,925,033 B2
(45) Date of Patent: Mar. 27, 2018

(54) SURGICAL IMPLANT DEVICES AND METHODS FOR THEIR MANUFACTURE AND USE

(71) Applicant: Edwards Lifesciences CardiAQ LLC, Irvine, CA (US)

(72) Inventors: Richard George Cartledge, Boca Raton, FL (US); John P. Cartledge, Boca Raton, FL (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 0 days.

(21) Appl. No.: 15/213,125

(22) Filed: Jul. 18, 2016

(65) Prior Publication Data
US 2016/0324625 A1    Nov. 10, 2016

Related U.S. Application Data

(62) Division of application No. 12/822,291, filed on Jun. 24, 2010, now Pat. No. 9,408,607.
(Continued)

(51) Int. Cl.
| *A61F 2/06* | (2013.01) |
| *A61B 17/115* | (2006.01) |
| *A61F 2/07* | (2013.01) |
| *A61B 17/072* | (2006.01) |
| *A61F 2/954* | (2013.01) |
| *A61F 2/958* | (2013.01) |
| *A61F 2/966* | (2013.01) |

(Continued)

(52) U.S. Cl.
CPC .......... *A61F 2/07* (2013.01); *A61B 17/07207* (2013.01); *A61B 17/115* (2013.01); *A61F 2/06* (2013.01); *A61F 2/848* (2013.01); *A61F 2/89* (2013.01); *A61F 2/954* (2013.01); *A61F 2/958* (2013.01); *A61F 2/966* (2013.01); *A61B 17/1155* (2013.01); *A61B 2017/07228* (2013.01); *A61B 2017/1157* (2013.01); *A61F 2/90* (2013.01); *A61F 2002/061* (2013.01); *A61F 2002/077* (2013.01); *A61F 2002/8483* (2013.01); *A61F 2002/8486* (2013.01); *A61F 2002/9534* (2013.01); *A61F 2220/0016* (2013.01); *A61F 2250/001* (2013.01)

(58) Field of Classification Search
CPC ........ A61F 2/07; A61F 2/89; A61F 2002/075; A61F 2/90; A61F 2/954; A61F 2002/077; A61F 2250/0039; A61F 2220/0016; A61F 2002/9511; A61F 2/06; A61F 2/848; A61F 2/966; A61F 2002/8483; A61F 2250/0069
See application file for complete search history.

(56) References Cited

U.S. PATENT DOCUMENTS

| 5,617,878 | A | * | 4/1997 | Taheri | ...................... | A61B 8/12 128/898 |
| 2002/0077695 | A1 | * | 6/2002 | Swanson | ................... | A61F 2/88 623/1.23 |
| 2006/0212113 | A1 | * | 9/2006 | Shaolian | ................... | A61F 2/07 623/1.35 |

* cited by examiner

*Primary Examiner* — Ann Schillinger
(74) *Attorney, Agent, or Firm* — Klarquist Sparkman, LLP; AnneMarie Kaiser

(57) ABSTRACT

This disclosure is directed toward sealable and repositionable implant devices that are provided with one or more improvements that increase the ability of implants such as endovascular grafts to be precisely deployed or re-deployed, with better in situ accommodation to the local anatomy of the targeted recipient anatomic site, and/or with the ability for post-deployment adjustment to accommodate anatomic changes that might compromise the efficacy of the implant.

20 Claims, 17 Drawing Sheets

Related U.S. Application Data

(60) Provisional application No. 61/222,646, filed on Jul. 2, 2009.

(51) Int. Cl.
*A61F 2/89* (2013.01)
*A61F 2/848* (2013.01)
*A61F 2/90* (2013.01)
*A61F 2/95* (2013.01)

SURGICAL IMPLANT DEVICES AND METHODS FOR THEIR MANUFACTURE AND USE

CROSS REFERENCE TO RELATED APPLICATION

This application is a divisional of copending U.S. patent application Ser. No. 12/822,291, filed on Jun. 24, 2010 (which application claims priority to U.S. Provisional Application Ser. No. 61/222,646, filed on Jul. 2, 2009), the entire disclosures of which are hereby incorporated herein by reference in their entireties.

FIELD OF THE INVENTION

The present disclosure relates to the field of surgical implant devices and method for their manufacture and use. In particular, this disclosure relates to medical devices applicable to vascular surgery and the treatment of aneurysms or other luminal defects in other anatomic conduits.

BACKGROUND OF THE INVENTION

Medical and surgical implants are often placed in anatomic spaces where it is desirable for the implant to conform to the unique anatomy of the targeted anatomic space to secure a seal therein, preferably without disturbing or distorting the unique anatomy of said targeted anatomic space.

While the lumens of most hollow anatomic spaces are ideally circular, in fact the cross-sectional configurations of most anatomic spaces are at best ovoid, and may be highly irregular. Lumenal irregularity may be due to anatomic variations and/or to pathologic conditions that may change the shape and topography of the lumen and its associated anatomic wall.

Examples of anatomic spaces where such implants may be deployed include, but are not limited to, blood vessels, the heart, other vascular structures, vascular defects, the trachea, the oropharynx, the esophagus, the stomach, the duodenum, the ileum, the jejunum, the colon, the rectum, ureters, urethras, fallopian tubes, biliary ducts, pancreatic ducts, or other anatomic structures containing a lumen used for the transport of gases, blood, or other liquids or liquid suspensions within a mammalian body.

Among vascular effects that are addressed by some preferred embodiments of the present disclosure are thoracic and abdominal aortic aneurysms.

In order for a patient to be a candidate for existing endograft methods and technologies, a proximal neck of at least 15 mm of normal aorta must exist between the origin of the most inferior renal artery and the origin of the aneurysm in the case of abdominal aneurysms or the left subclavian artery for thoracic aortic aneurysms in order to permit an adequate seal. Similarly, at least 15 mm of normal vessel must exist distal to the distal extent of the aneurysm for an adequate seal to be achieved.

Migration of existing endografts has also been a significant clinical problem, potentially causing leakage and re-vascularization of aneurysms and/or compromising necessary vascular supplies to arteries such as the carotid, subclavian, renal, or internal iliac vessels. This problem has been partially addressed by some existing endograft designs, in which barbs or hooks have been incorporated to help retain the endograft at its intended site. However, these existing endograft designs are not removable and repositionable once they are deployed. Thus, once such an endograft has been placed, open surgery is necessary if there is failure due to leakage or undesired occlusion of other vascular structures.

Because of the limitations imposed by existing vascular endograft devices and endovascular techniques, approximately eighty percent of abdominal and thoracic aneurysms repaired in the U.S. are still managed though open vascular surgery, instead of the lower morbidity of the endovascular approach.

SUMMARY OF THE INVENTION

Implant devices according to the present disclosure are provided with one or more improvements that increase the ability of such an implant to be precisely deployed or re-deployed, with better in situ accommodation to the local anatomy of the targeted anatomic site, and/or with the ability for post-deployment adjustment to accommodate anatomic changes that might compromise the efficacy of the implant.

One aspect of the present disclosure is directed towards novel designs for endovascular implant grafts, and methods for their use for the treatment of aortic aneurysms and other structural vascular defects. A sealable, repositionable endograft system for placement in a blood vessel is disclosed, in which an endograft implant comprises a non-elastic tubular implant body with an elastic proximal ends and an elastic distal end(s). Both the elastic proximal and distal ends in an implant according to the present disclosure further comprise one or more circumferential sealable collars and one or more variable sealing device, capable of controllably varying the expanded diameter of said collar upon deployment to achieve the desired seal between the collar and the vessel's inner wall. An endovascular implant according to the present disclosure further comprises a central lumen and one or more control leads extending distally from releasable connections with each variable sealing device. Embodiments of endovascular implants according to the present disclosure may further be provided with retractable retention tines or other retention devices allowing an implant to be repositioned before final deployment. An endograft system according to the present disclosure further comprises a delivery catheter with an operable tubular sheath, capable of housing a folded or compressed endograft implant prior to deployment and capable of retracting or otherwise opening in at least its proximal end to allow implant deployment, said sheath sized and configured to allow its placement via a peripheral arteriotomy site, and of appropriate length to allow its advancement into the thoracic or abdominal aorta, as required for a specific application.

Post-implantation remodeling of the aortic neck proximal to an endovascular graft (endograft) has been reported. While this phenomenon may be due to aortic wall injury caused by the over-dilatation (typically 110%) of the aorta to deploy the metallic lattice that supports such endografts, existing endograft technology does not allow for the management of this condition without placement of an additional endograft sleeve to cover the remodeled segment, again requiring the over-dilatation for deployment.

Endografts of the present disclosure do not require balloon over-dilatation for their deployment. Moreover, the improvements in implant design described herein allow for better accommodation by the implant of the local anatomy, as opposed to altering the local anatomy to conform to the implant as is the presently accepted practice. Finally, implants with improvements of the present disclosure may be provided with means to change the implant configuration post-initial deployment, allowing for manual adaptation to any future anatomic remodeling at the implantation site.

The preceding description is presented only as an exemplary application of the devices and methods according to the present disclosure.

DETAILED DESCRIPTION OF DISCLOSED EMBODIMENTS

Figure 1A:
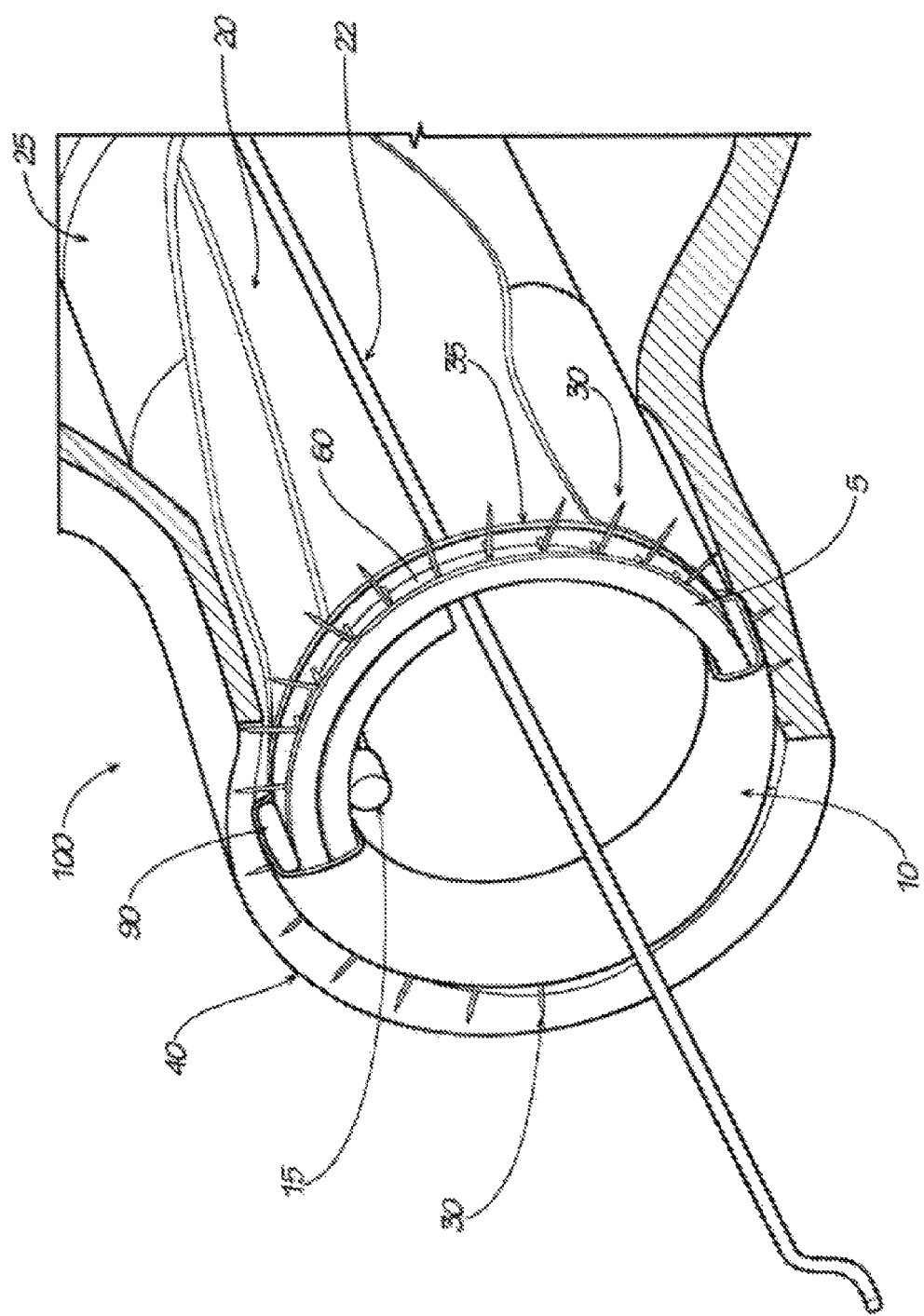
FIG. 1A is a perspective view of an embodiment of an implant interface according to the present disclosure.

The present disclosure may be understood more readily by reference to the following detailed description of the preferred embodiments described herein and the examples included herein. However, before the preferred embodiments of the devices and methods according to the present disclosure are described, it is to be understood that this disclosure is not limited to the exemplary embodiments described within this disclosure, and the numerous modifications and variations therein that will be apparent to those skilled in the art remain within the scope of the disclosure provided herein. It is also to be understood that the terminology used herein is for the purpose of describing specific embodiments only and is not intended to be limiting.

Unless otherwise noted, the terms used herein are to be understood according to conventional usage by those of ordinary skill in the relevant art. In addition to the definitions of terms provided below, it is to be understood that as used in the specification and in the claims, "a" or "an" can mean one or more, depending upon the context in which it is used.

Certain aspects of the present disclosure are directed towards novel designs for sealable and repositionable endovascular implant grafts, and methods for their use for the treatment of aortic aneurysms and other structural vascular defects.

In an exemplary embodiment according to the present disclosure, a sealable vascular endograft system for placement in a vascular defect is provided, comprising an elongated main implant delivery catheter with an external end and an internal end for placement in a blood vessel with internal walls. In such an exemplary embodiment, the main implant delivery catheter further comprises a main implant delivery catheter sheath which may be openable or removable at said internal end and a main implant delivery catheter lumen containing within a compressed or folded endovascular implant. Further in such an exemplary embodiment, an endovascular implant comprises a non-elastic tubular implant body with an elastic proximal end terminating in a proximal sealable circumferential collar controlled by a proximal variable sealing device which is operated by a proximal control lead that traverses said main implant delivery catheter and exits at said external end for interface by an operator, such that said proximal sealable circumferential collar may be expanded or contracted by said operator to achieve a fluid-tight seal between said proximal sealable circumferential collar and the internal walls of said blood vessel proximal to said vascular defect. Moreover, in such an exemplary embodiment, an endovascular implant further comprises a non-elastic tubular implant body with an elastic distal end terminating in a distal sealable circumferential collar controlled by a distal variable sealing device which is operated by a distal control lead that exits said main implant delivery catheter at said external end for interface by an operator, such that said distal sealable circumferential collar may be expanded or contracted by said operator to achieve a fluid-tight seal between said distal sealable circumferential collar and the internal walls of said blood vessel distal to the vascular defect.

In an alternate exemplary embodiment of the present disclosure, an endovascular implant comprises a non-elastic tubular implant body with an elastic proximal end terminating in a proximal sealable circumferential collar controlled by a proximal variable sealing device which is operated by a proximal control lead that traverses said main implant delivery catheter and exits at said external end for interface by an operator, such that said proximal sealable circumferential collar may be expanded or contracted by said operator to achieve a fluid-tight seal between said proximal sealable circumferential collar and the internal walls of said blood vessel proximal to said vascular defect. Moreover, in such an exemplary embodiment, an endovascular implant further comprises a non-elastic tubular implant body with an elastic distal end with a distal elastic circumferential collar of an expandable mesh or lattice formation that may be expanded by intralumenal balloon dilatation by said operator to achieve a fluid-tight seal between said distal elastic circumferential collar and the internal walls of said blood vessel distal to the vascular defect. In such an embodiment, particularly in the iliac arteries, the distal aspect of the endograft requires less pressure for an effective seal, and more length of arterial wall is usually available to allow an expandable mesh collar to be employed, compared with the proximal seal which often may be required to accommodate a shortened and/or angulated aortic neck.

In yet another embodiment of the present disclosure, the distal seal, particularly in the iliac arteries, may be effected using a self-expanding mesh endoskeleton or exoskeleton collar attached to the elastic distal end, provided such that the self-expanding mesh endoskeleton or exoskeleton collar is designed such that longitudinal traction on the deployed mesh causes the mesh to elongate and reduce its circumference. This would allow instrumentation to be inserted such as a hook that could adjust the distal seal location post implant deployment. Again, in such an embodiment, particularly in the iliac arteries, the distal aspect of the endograft requires less pressure for an effective seal, and more length of arterial wall is usually available to allow a self-expanding mesh endoskeleton or exoskeleton collar to be employed, compared with the proximal seal which often must accommodate a shortened and/or angulated aortic neck.

Exemplary endografts of the present disclosure comprising self-expanding mesh endoskeleton or exoskeleton collar may further comprise retention tines of any shape with or without barbs for better retention against the receiving vessel walls. Moreover, the retention tines in such endografts of the present disclosure may be provided as separate components that are affixed to the self-expanding mesh endoskeleton or exoskeleton collars, or they may be fabricated as integral components thereof.

In a further exemplary embodiment according to the present disclosure, an implant interface is provided for a sealable attachment of an implant to a wall within the lumen of a blood vessel or other anatomic conduit.

In a yet further exemplary embodiment according to the present disclosure, an implant interface is provided for a sealable attachment of an implant to a wall within the lumen of a blood vessel or other anatomic conduit, wherein the sealable attachment provides for auto-adjustment of the seal while maintaining wall attachment to accommodate post-implantation wall remodeling.

In a still further exemplary embodiment according to the present disclosure, an implant interface is provided for a sealable attachment of an implant to a wall within the lumen of a blood vessel or other anatomic conduit, wherein the sealable attachment provides for a re-docking mechanism to allow post-implantation correction of seal defects.

Yet other exemplary embodiments of endografts and endograft delivery systems according to the present disclosure have steering mechanisms that allow an operator to remotely angulate the implant as desired for difficult anatomic site requirements. Still other exemplary embodiments of endografts and endograft delivery systems according to the present disclosure serve as universal endograft cuffs, being first placed to offer their advantageous anatomic accommodation capabilities, and then serving as a recipient vessel for other endografts, including conventional endografts.

Further exemplary embodiments of endografts according to the present disclosure provide for endovascular treatment of complex anatomic vascular pathologies involving the aortic arch including aneurysms and dissecting aneurysms of the aortic arch.

Referring now in more detail to the drawings, in which like numerals indicate like elements throughout the several views, FIG. 1A shows a proximal circumferential sealable implant interface 100 according to the present disclosure, comprising a sealer belt 60, sealer belt channel side walls 5 provided in an overlapping loop and with a sealer belt channel 35 therewithin, a plurality of retention tines 30 and a compressive foam gasket 90 within said sealer belt channel 35, and a sealing device housing 15, all contained within an elastic sealable collar 10 which is shown in the embodiment of FIG. 1A joined to and continuous with a tubular graft main body 25.

FIG. 1A further shows the proximal circumferential sealable implant interface 100 in place within the lumen defined by an aortic wall 40, and with an injection dye catheter 22 traversing the sealable implant interface 100 and adjoining tubular graft main body 25. Imbedded retention tines 30 are shown within the aortic wall 40. Also shown in FIG. 1A is a control lead 20 extending distally from its attachment to the sealing device housing 15 to exit through an arteriotomy site for operative control by an operator (not shown in FIG. 1A).

In alternate embodiments of the present disclosure not shown in FIGS. 1A-11 herein, a circumferential sealable implant may comprise a freestanding implant which is coupled with or otherwise affixed to a tubular graft at the time of implantation.

Figure 1B:
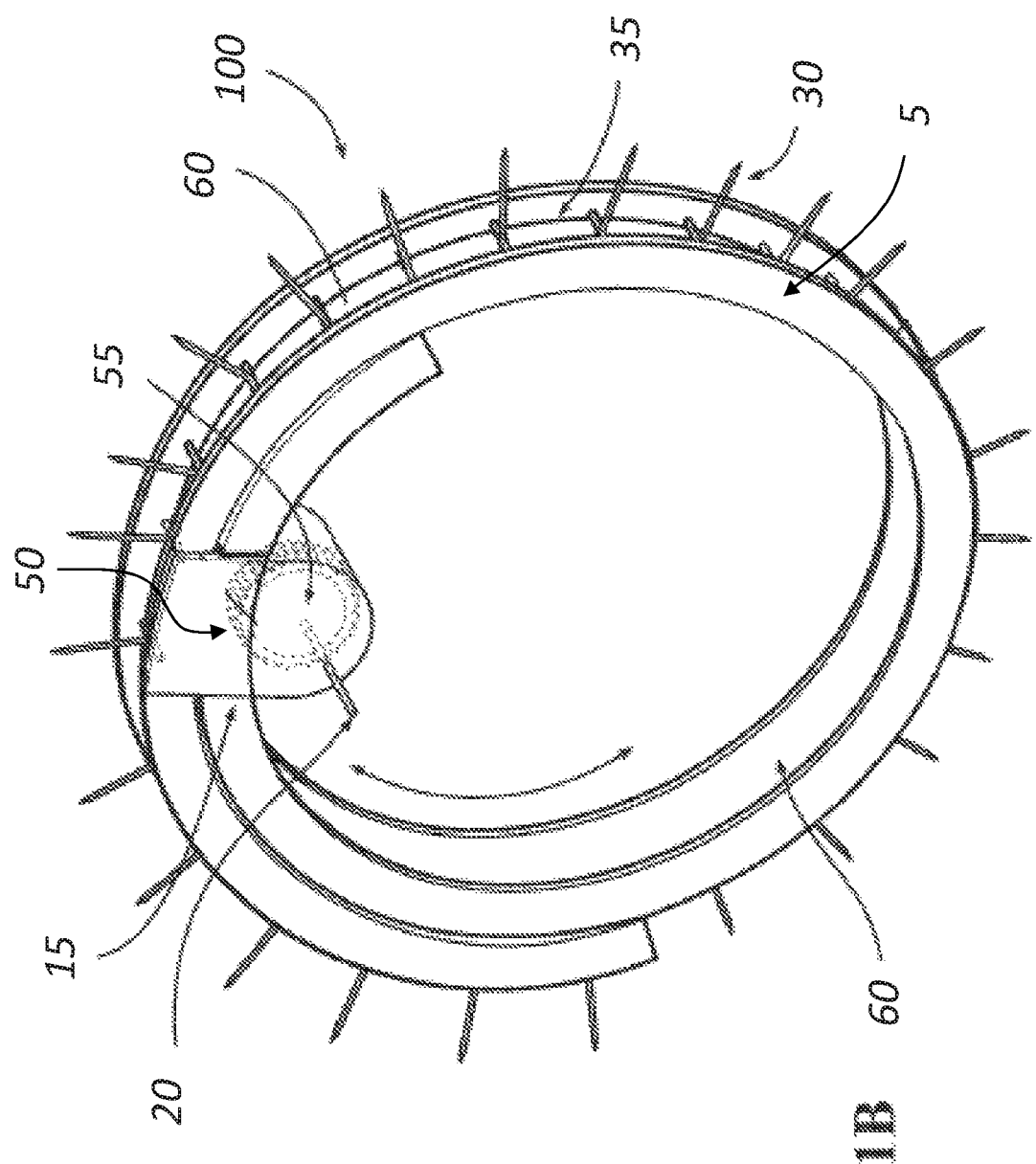
FIG. 1B is a detailed view of an embodiment of an implant interface according to the present disclosure.

FIG. 1B shows a detailed view of one embodiment of a sealable implant interface according to the present disclosure. In FIG. 1B, the sealable implant interface 100 comprises a sealer belt 60 and sealer belt channel side walls 5 provided in an overlapping loop and with a sealer belt channel 35 therewithin to contain a plurality of retention tines 30 and a compressive foam gasket [not shown in FIG. 1B], and a sealing device housing 15. Within said sealing device housing 15, a sealer gear 50 is rotatably mounted to interface with sealer gear retainment slots [not shown in FIG. 1B] located on the sealer belt 60, such that rotation of the sealer gear 50 by operator action on an attached control lead 20 may cause movement of said sealer belt 60 with respect to said sealer gear 50.

In the embodiment shown in FIG. 1B, the sealer gear 50 is further provided with a spring interface 55 with said control lead 20, such that an operator first depresses the spring interface 55 with said control lead 20 to allow rotation of the sealer gear 50 and resultant movement of the sealer belt 60. When the spring interface 55 is not depressed, rotation of the sealer gear 50 is blocked by action of a locking member (not shown in FIG. 1B).

Figure 2:
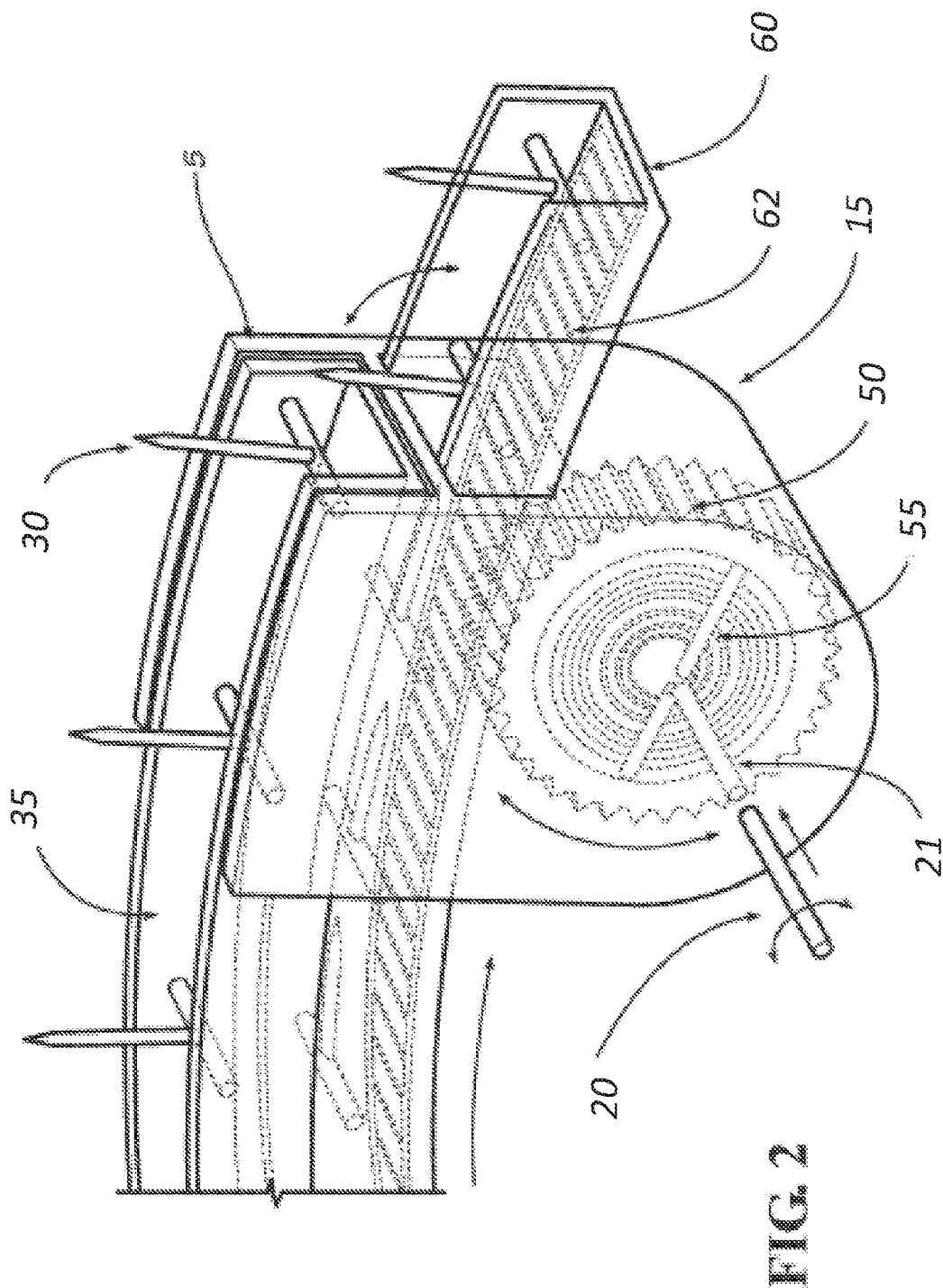
FIG. 2 is a detailed view of an embodiment of an implant interface with a coil spring drive gear design according to the present disclosure.

FIG. 2 provides a more detailed view of an embodiment of the coil spring drive gear design of the sealer gear mechanism described in FIG. 1B. FIG. 2 shows a sealer belt 60, sealer belt channel side walls 5 provided in an overlapping loop and with a sealing device housing 15 and a sealer belt channel 35 with a plurality of uniformly distributed sealer gear retainment slots 62 therewithin configured to receive the teeth of a sealer gear 50. The sealer belt channel 35 is provided to contain a plurality of retention tines 30 and a compressive foam gasket [not shown in FIG. 2].

The sealer belt 60 as shown in FIG. 2 and in all other embodiments of the present disclosure may be fabricated of any suitably strong biocompatible material, including, but not limited to titanium, stainless steel, cobalt chromium alloys, other metals, other metal alloys, plastics, or ceramics.

FIG. 2 further illustrates an embodiment in which the retention tines 30 are pivotably mounted within said sealer belt channel 35 to permit their folding within said channel 35 within the overlapping segments of the sealer belt 60.

The coil spring drive gear design of the sealer gear 55 is also detailed in FIG. 2. Pressure transmitted by an operator through a control lead 20 to the central axel 21 of the sealer gear 50 first depresses the spring interface 55 within said sealer gear, allowing the sealer gear to rotate upon subsequent receipt of rotational forces applied by said user to said control lead 20.

Figure 3:
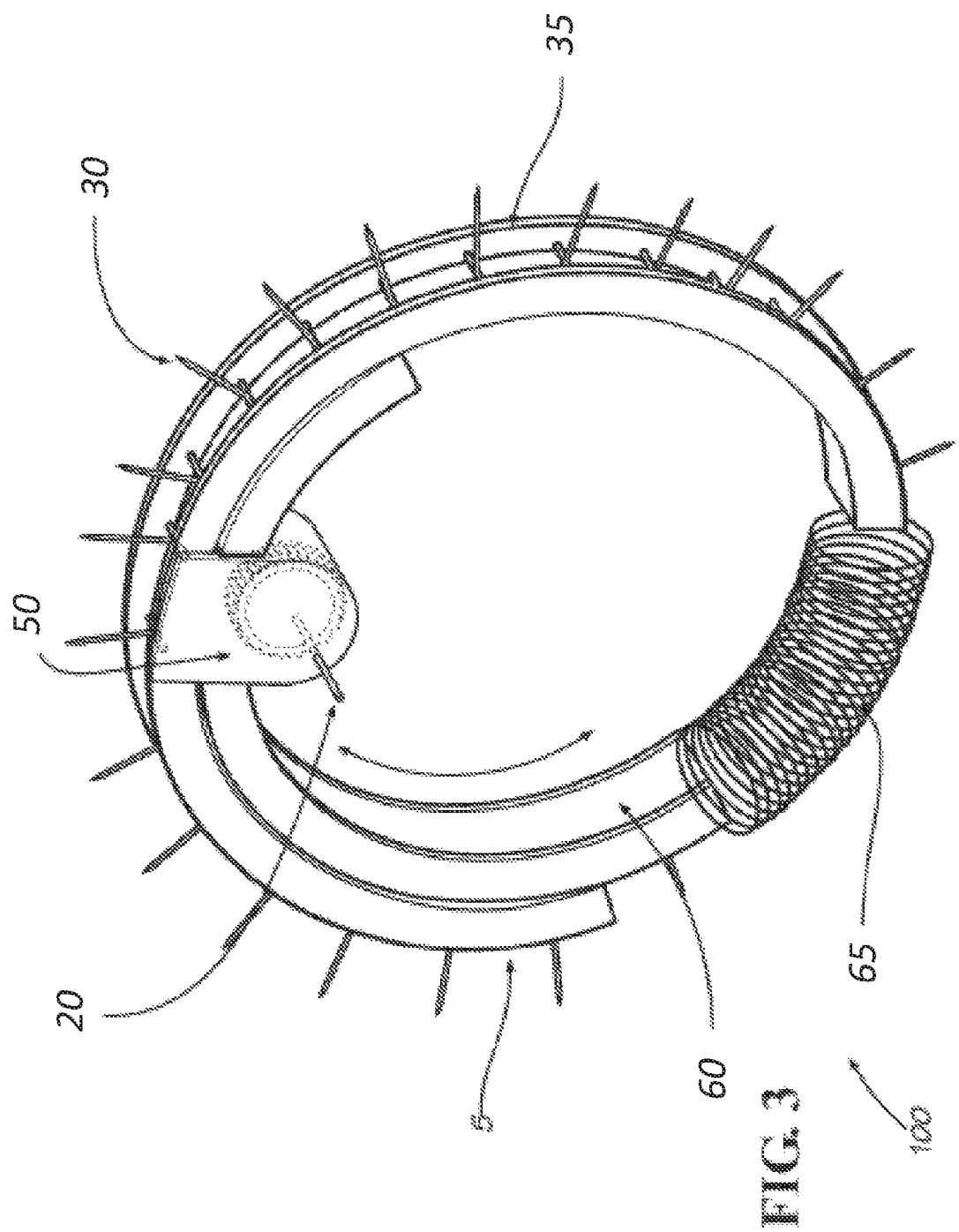
FIG. 3 is a perspective view of an embodiment of an implant interface with an uncompressed spring interposition mechanism according to the present disclosure.

FIG. 3 shows a perspective view of an embodiment of an implant interface with an uncompressed spring interposition mechanism according to the present disclosure. The exemplary sealable implant interface 100 as shown in FIG. 3 resembles the embodiment of FIG. 1B, with a sealer belt 60, sealer belt channel side walls 5 provided in an overlapping loop and with a sealer belt channel 35 therewithin to contain a plurality of retention tines 30 and a compressive foam gasket [not shown in FIG. 1B], and a sealing device housing 15. Within said sealing device housing 15, a sealer gear 50 is rotatably mounted to interface with sealer gear retainment slots [not shown in FIG. 3] located on the sealer belt 60, such that rotation of the sealer gear 50 by operator action on an attached control lead 20 may cause movement of said sealer belt 60 with respect to said sealer gear 50.

In the embodiment of FIG. 3, however, a segment of sealer belt 60 is replaced by an interposed and attached coiled spring 65 shown in a decompressed state. In use, motion imparted to the sealer gear 50 of the sealable implant interface 100 of FIG. 3 may serve to compress or decompress the spring 65.

Figure 4:
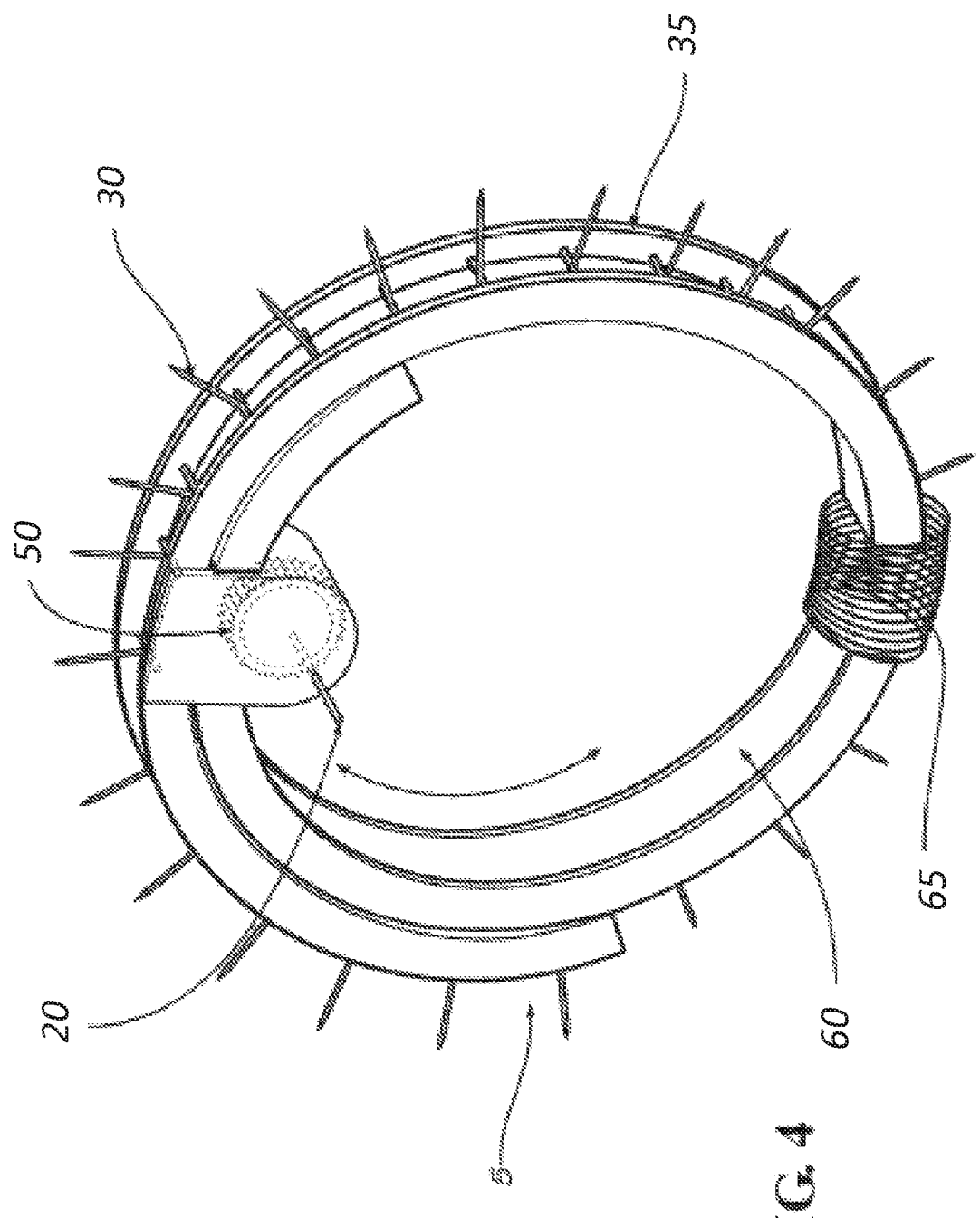
FIG. 4 is a perspective view of an embodiment of an implant interface with a compressed spring-tine mechanism according to the present disclosure.

FIG. 4 shows the same embodiment of an implant interface as FIG. 3, but with a compressed spring-tine mechanism. Compression of the spring 65 creates and maintains radial tension that allows such an embodiment of the present disclosure to automatically provide a fixed amount of adjustment in the event of post-implantation remodeling and dilation of the aorta or recipient blood vessel or anatomic conduit.

Figure 5:
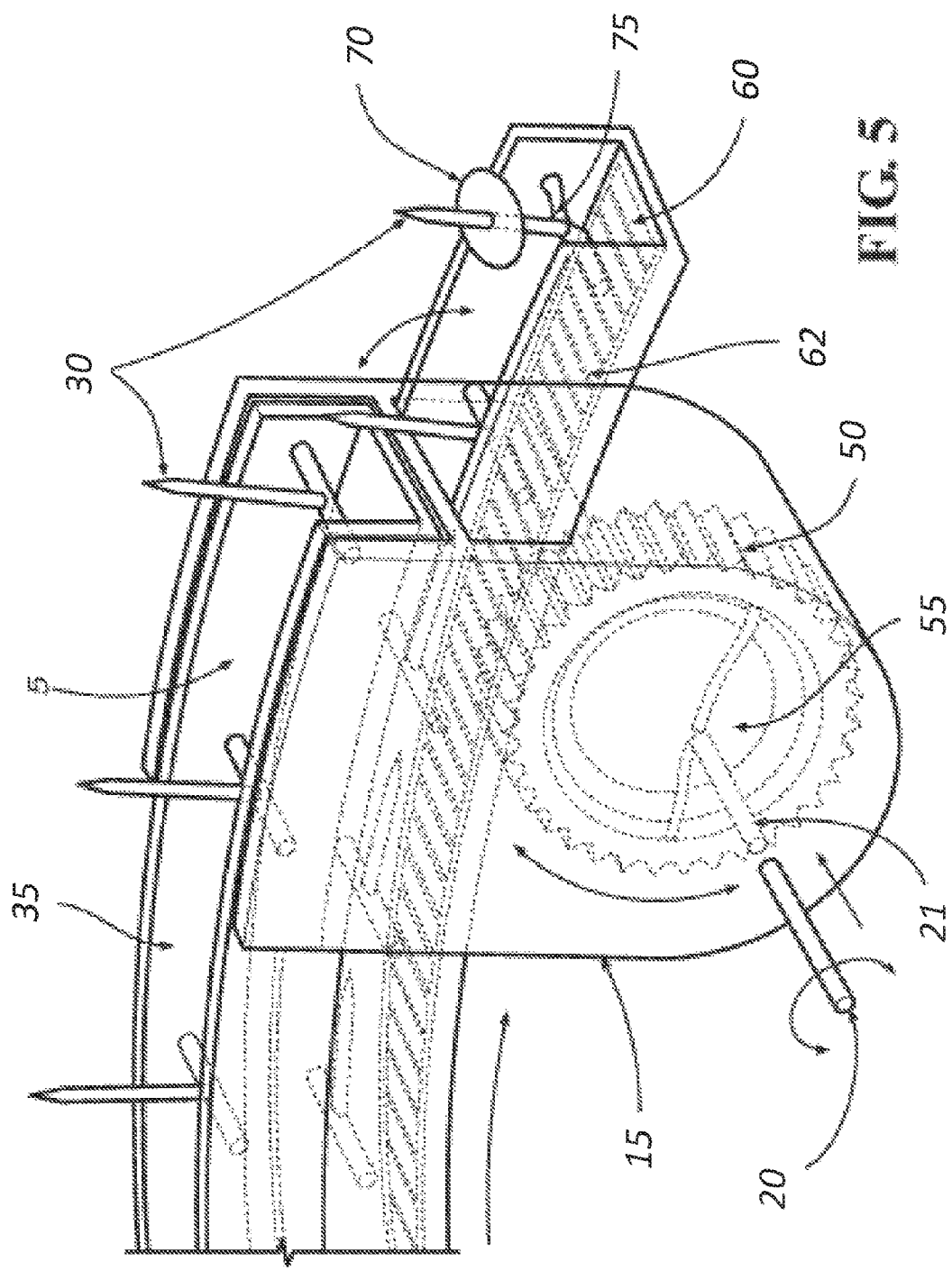
FIG. 5 is a detailed view of an embodiment of an implant interface with an electromagnetic re-docking mechanism and spring-loaded remodeling attachment members according to the present disclosure.

FIG. 5 provides a detailed view of an alternate embodiment of an implant interface with an electromagnetic re-docking mechanism and spring-loaded remodeling attachment members according to the present disclosure. In FIG. 5 a detail of an implant interface comprises sealer belt 60 with side walls 5 provided in an overlapping loop and with a sealer belt channel 35 therewithin to contain a plurality of retention tines 30, a plurality of uniformly distributed sealer gear retainment slots 62 therewithin configured to receive the teeth of a sealer gear 50, and a compressive foam gasket [not shown in FIG. 5], and a sealing device housing 15 containing a sealer gear 50.

Also in FIG. 5, a coil spring drive gear design of the sealer gear 55 is also detailed. Pressure transmitted by an operator through a control lead 20 attached to the central axel 21 of the sealer gear 50 first depresses a spring interface 55 within said sealer gear, allowing the sealer gear to rotate upon subsequent receipt of rotational forces applied by said user to said control lead 20.

Furthermore, FIG. 5 shows one of more retention tines 30 pivotably attached to the side walls 63 of the sealer belt 60, such that advancement or retraction of the sealer belt 60 by rotational action of the sealer gear causes said tines to either extend outwardly from said sealer belt 60 or retract within the sealer belt channel 35 when the circumference of the sealer belt 60 is made smaller. In the embodiment shown in FIG. 5, one or more of the retention tines 30 may be further provided with a tine limiter element 70 which serves to limit the depth to which the retention tine 30 may be extended into the wall of the recipient blood vessel or other anatomic conduit.

In addition, as shown in FIG. 5, one or more of the retention tines 30 may be attached to the sealer belt 60 with a pre-tensioned tine mounting element 75 (also called pre-tensioned spring element 75, throughout) that serves to exert an outward radial force on its related retention tine 30 upon deployment.

FIGS. 6A-6D provides detailed views of several exemplary embodiments of spring-loaded remodeling attachment members according to the present disclosure.

Figure 6A:
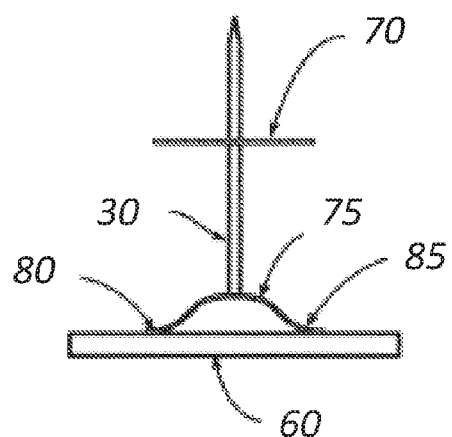
FIGS. 6A-6D are detailed views of several exemplary embodiments of spring-loaded remodeling attachment members according to the present disclosure.

FIG. 6A shows a sealer belt 60 with a retention tine 30 mounted at an erect angle thereto, said retention tine 30 further comprising a tine limiter element 70 which serves to limit the depth to which the retention tine 30 may be extended into the wall of the recipient blood vessel or other anatomic conduit.

Figure 6B:
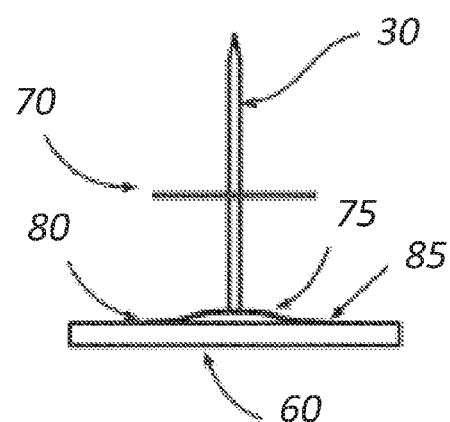

In FIGS. 6A and 6B, said retention tine 30 may be welded or otherwise affixed to a pre-tensioned tine mounting element 75 that serves to exert an outward radial force on its related retention tine 30 upon deployment. As shown in FIGS. 6A and 6B, the pre-tensioned tine mounting element 75 has two ends 80 and 85. In the embodiment of the present disclosure as shown in FIGS. 6A and 6B, end 80 is welded or permanently affixed to the surface of the sealer band 60 (also called sealer belt 60) and end 85 is free to slide across the surface of the sealer band 60 when longitudinal force is applied to the associated retention tine 30.

Figure 6C:
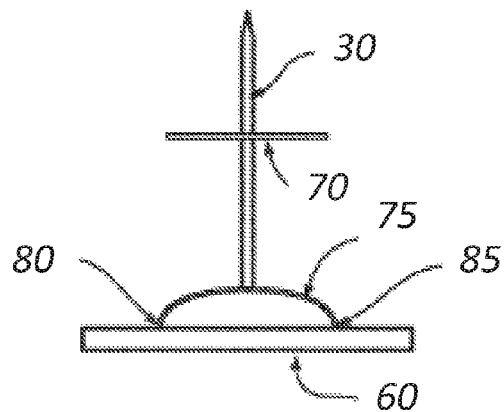
Figure 6D:
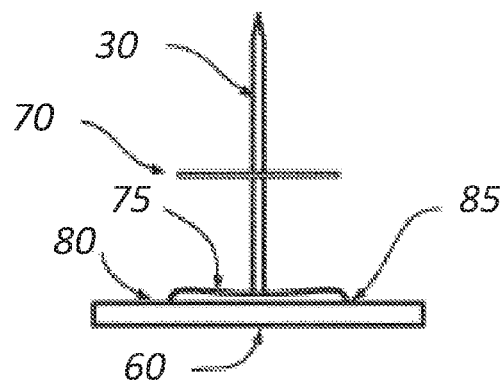

In FIGS. 6C and 6D, said retention tine 30 may be welded or otherwise affixed to a pre-tensioned tine mounting element 75 that serves to exert an outward radial force on its related retention tine 30 upon deployment. As shown in FIGS. 6C and 6D, the pre-tensioned tine mounting element 75 has two ends 80 and 85. In the embodiment of the present disclosure as shown in FIGS. 6C and 6D, both ends 80 and 85 are welded or permanently affixed to the surface of the sealer band 60.

The pre-tensioned tine mounting elements 75 as shown in FIGS. 6A-6D maintain radial tension that allows such an embodiment of the present disclosure to automatically provide a fixed amount of adjustment in the event of post-implantation remodeling and dilation of the aorta or recipient blood vessel or anatomic conduit.

Figure 7A:
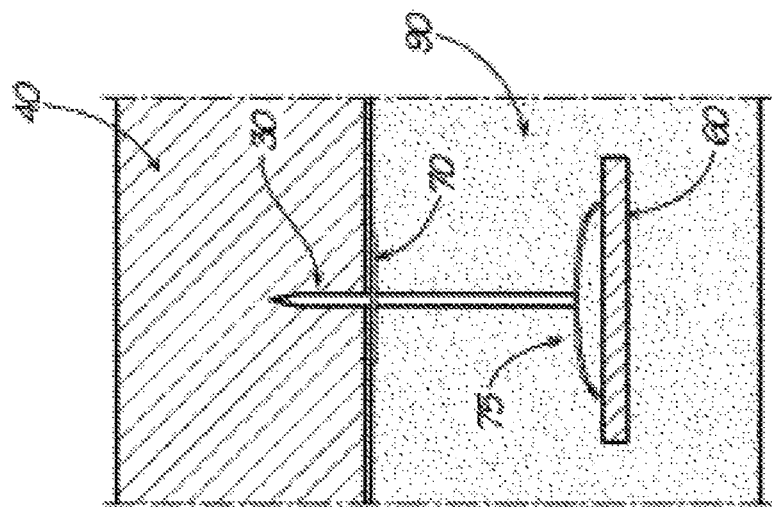
FIG. 7A is a detailed cross sectional view of an exemplary embodiment of spring-loaded remodeling attachment member contained within an uncompressed foam gasket according to the present disclosure.
Figure 7B:
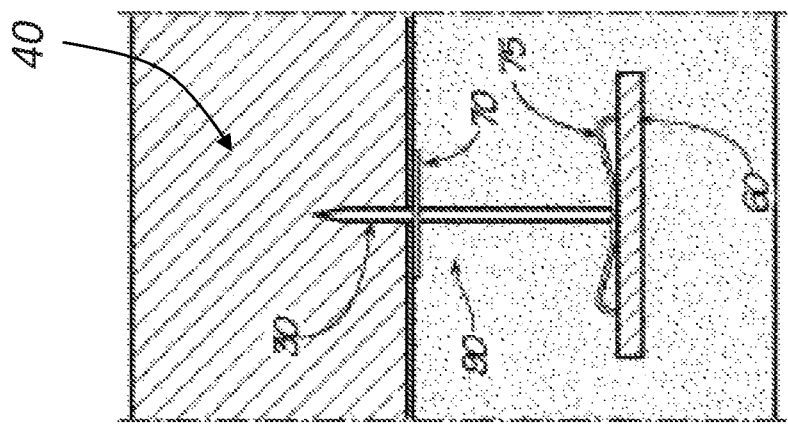
FIG. 7B is a detailed cross sectional view of an exemplary embodiment of spring-loaded remodeling attachment member deployed into an aortic wall through a compressed foam gasket with a spring-loaded remodeling attachment at full tension according to the present disclosure.
Figure 7C:
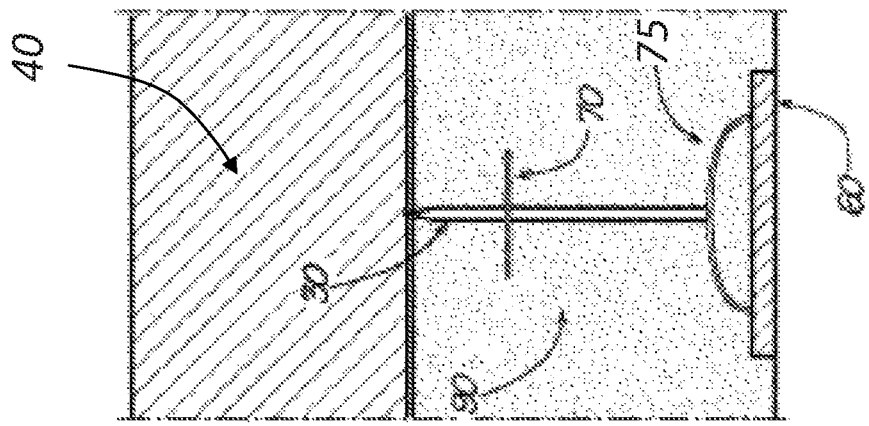
FIG. 7C is a detailed cross sectional view of an exemplary embodiment of spring-loaded remodeling attachment member deployed into an aortic wall through a compressed foam gasket with a spring-loaded remodeling attachment at full extension to accommodate aortic remodeling according to the present disclosure.

FIGS. 7A-7C show the relationship among the retention tines 30, pre-tensioned spring elements 75, compressible foam gasket 90, and aortic wall 40 in an exemplary embodiment according to the present disclosure.

FIG. 7A is a detailed cross sectional view of an exemplary embodiment of spring-loaded remodeling attachment member contained within an uncompressed foam gasket according to the present disclosure. In FIG. 7A, a retention tine 30 with a tine limiter element 70 is shown attached to a sealer band 60 by a pre-tensioned spring element 75. As shown in FIG. 7A, the retention tine is completely covered by the foam gasket 90 in an uncompressed or pre-deployment condition.

Upon deployment, as shown in FIG. 7B, the foam gasket 90 is compressed between the sealer band 60 and the aortic wall 40, with penetration of the retention tine 30 into the aortic wall 40. The extent of penetration of the retention tine 30 into the aortic wall 40 is limited by a tine limiter element 70 as shown In FIGS. 7B and 7C. FIG. 7B shows the pre-tensioned spring element 75 at maximal tension.

FIG. 7C is a detailed cross sectional view of the same exemplary embodiment as shown in FIG. 7B, with deployment of retention tines 30 into an aortic wall 40 through a compressed foam gasket 90 with full extension of the pre-tensioned spring element 75 to accommodate aortic remodeling according to the present disclosure.

The embodiments of the retention tines as shown in the present drawings show the retention tines to be substantially straight, and at about ninety degree angles relative to the sealer band 60. However, other embodiments on the present disclosure may comprise curved or otherwise angled retention tines, or retention tines that may be constructed of Nitinol or other shape/memory materials so that such retention tines become angled or curved upon deployment to further strengthen the attachment of said retention tines to the aortic walls or other recipient anatomic tissues. The retention tines in various embodiments of endografts of the present disclosure may be of any cross-sectional shape, and may further be terminally rounded, sharpened, tapered, or hooked, In still further embodiments of the retention tines in endografts of the present disclosure, the retention tines may be barbed or non-barbed. Furthermore, the number of retention tines associated with a sealer band in various embodiments of the present disclosure may vary. Preferred embodiments of sealer bands or sealable circumferential collars of this disclosure comprise at least two retention tines. Moreover, the retention tines in endografts of the present disclosure may be provided as separate components that are affixed to the sealer bands or sealable circumferential collars, or they may be fabricated as integral components thereof.

FIGS. 8A-8D provide detailed views of several alternate exemplary embodiments of spring-loaded remodeling attachment members according to this disclosure.

Figure 8A:
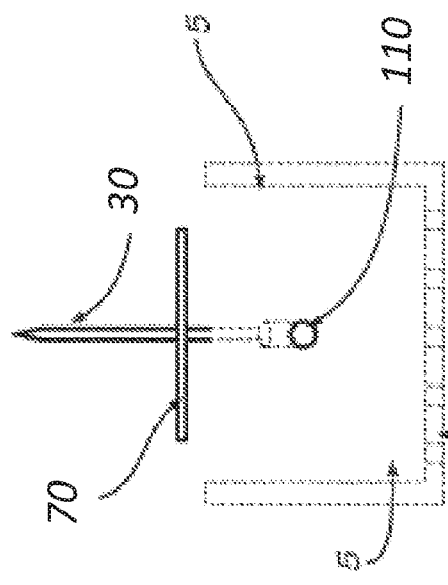
FIGS. 8A-8D are detailed views of several alternate exemplary embodiments of spring-loaded remodeling attachment members according to the present disclosure.

FIG. 8A shows a cross section of an embodiment of a sealer belt with attached retention tines according to the present disclosure. In FIG. 8A, a retention tine 30 with a tine limiter element 70 is affixed to a support element 105 which in turn is affixed to sealer belt channel side walls 5 which are connected to a sealer belt 60. Elements may be affixed in this and other embodiments of the present disclosure by any means, including but not limited to welding, cementing, or mechanical fixation. A support element 105 in various embodiments of the present disclosure may further be inserted into and retained in bores or detents in the sealer belt channel side walls 5 (not shown in FIG. 8A). Alternately still, in some embodiments of the present disclosure, a retention tine 30 may be cast or otherwise fabricated as a single unit with a support element 105.

In various embodiments of the present disclosure, a sealer belt 60 and sealer belt channel side walls 5 may form a channel of angles ranging from about 10.degree. to about 170.degree.; more preferably from about 40.degree. to about 140.degree.; and most preferably about 90.degree. In other embodiments of the present disclosure, a sealer belt 60 and sealer belt channel side walls 5 may form a continuous structure which may be circular, ovoid, semi-circular, or semi-ovoid on cross section.

Also, in various embodiments of this disclosure, the support element 105 may be a rigid structure or it may be a pre-tensioned spring. Similarly, in various embodiments of the present disclosure, the retention tine 30 may be straight (as shown in FIG. 8A) or it may be curved or helical in some or all its length. A retention tine 30 of the present disclosure may be fabricated from a shape memory material such as Nitinol or other metals, metal alloys, ceramics, plastics, or combinations thereof with shape memory characteristics to allow such a retention tine 30 to restore and maintain a desired shape upon its deployment.

Figure 8B:
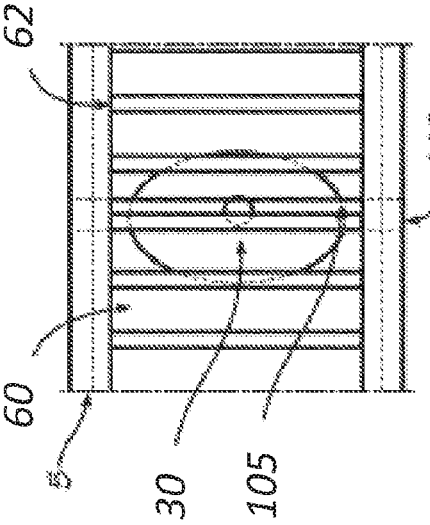

FIG. 8B shows a side view of the sealer belt with attached retention tines of FIG. 8A. In FIG. 8B, a retention bore 110 is shown in a sealer belt channel side wall 5 where it receives and retains the support element 105 and supports the retention tine 30 with a tine limiter element 70. Also in FIG. 8B, the sealer belt 60 is shown to comprise a plurality of uniformly distributed sealer gear retainment slots 62 therewithin configured to receive the teeth of a sealer gear [not shown in FIG. 8B].

Figure 8C:
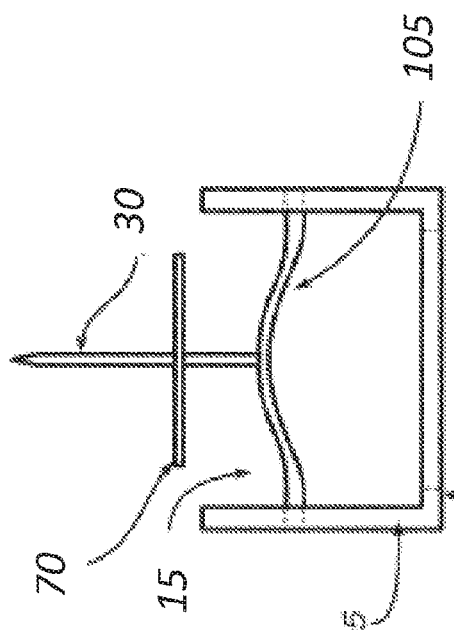

FIG. 8C shows a top view of FIG. 8A, with a retention tine 30 with a tine limiter element 70 affixed to a support element 105 which in turn is affixed to sealer belt channel side walls 5 which are connected to a sealer belt 60 with a plurality of uniformly distributed sealer gear retainment slots 62.

Figure 8D:
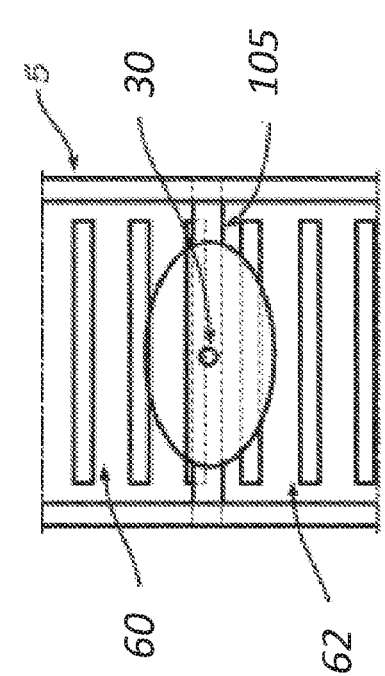

FIG. 8D similarly shows a top view of the sealer belt with attached retention tines of FIG. 8B, with a retention bore 110 shown in a sealer belt channel side wall 5 where it receives and retains the support element 105 and supports the retention tine 30 with a tine limiter element 70. Also in FIG. 8D, the sealer belt 60 is shown to comprise a plurality of uniformly distributed sealer gear retainment slots 62 therewithin configured to receive the teeth of a sealer gear [not shown in FIG. 8D].

Figure 9A:
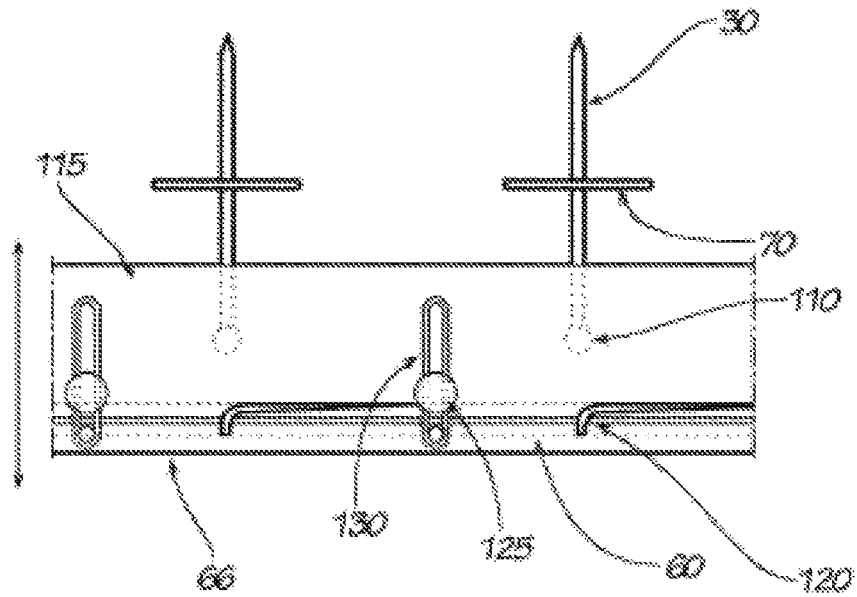
FIGS. 9A and 9B are detailed views of another exemplary embodiment of spring-loaded remodeling attachment members according to the present disclosure, in which the band containing attachment members is mounted to a fully compressed spring-tensioned suspension.
Figure 9B:
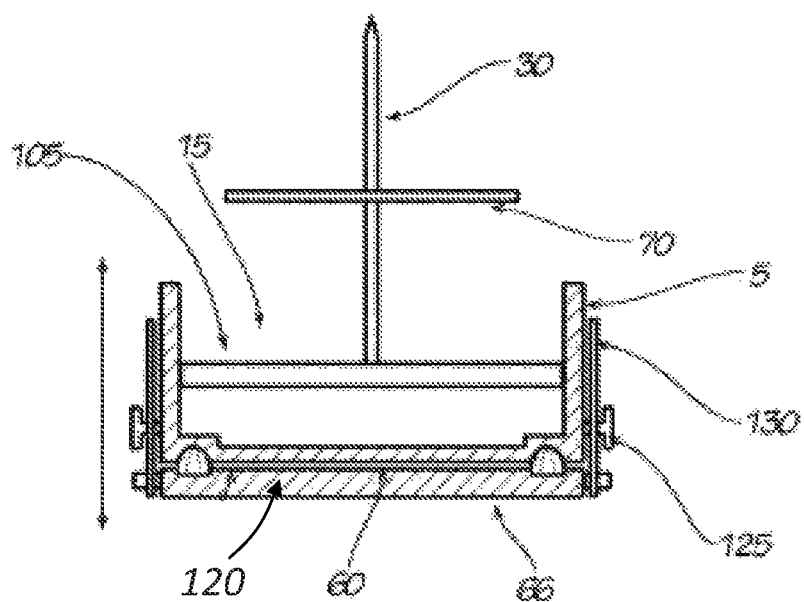

FIGS. 9A and 9B are detailed views of another exemplary embodiment of spring-loaded remodeling attachment members according to the present disclosure, in which the band containing attachment members is mounted to a spring-tensioned suspension. FIG. 9A is a lateral view of the same exemplary embodiment of spring-loaded remodeling attachment shown in cross section in FIG. 9B.

In FIGS. 9A and 9B, one or more retention tines 30 with tine limiter elements 70 are affixed to support elements 105 which in turn are affixed to sealer belt channel side walls 5 which are connected to a sealer belt 60. A retention bore 110 shown in a sealer belt channel side wall 5 where it receives and retains the support element 105 and supports the retention tine 30 with a tine limiter element 70.

In the exemplary embodiment shown in FIGS. 9A and 9B, Retention fasteners 125 affixed to the sealer belt channel side walls 5 are received and retained in slots in channel expansion elements 130. The channel expansion elements 130 are permanently affixed to a sealer belt expansion base 66, which may further be provided with a plurality of uniformly distributed sealer gear retainment slots 62 therewithin configured to receive the teeth of a sealer gear [not shown in FIG. 9A or B]. Separating the sealer belt 60 and sealer belt expansion base 66 are one or more expansion spring elements 120 which exert a spring-loaded tension between the sealer belt 60 and sealer belt expansion base 66. In FIGS. 9A and 9B, the one or more expansion spring elements 120 are shown in a compressed or non extended state, with close approximation between the sealer belt 60 and sealer belt expansion base 66.

Retention fasteners 125 as used in the present disclosure may be screws, rivets, pins, or other fasteners, and may be affixed to the sealer belt channel side walls 5 by welding, adhesives, screw threads rivets, or other known means of attaching.

Figure 10A:
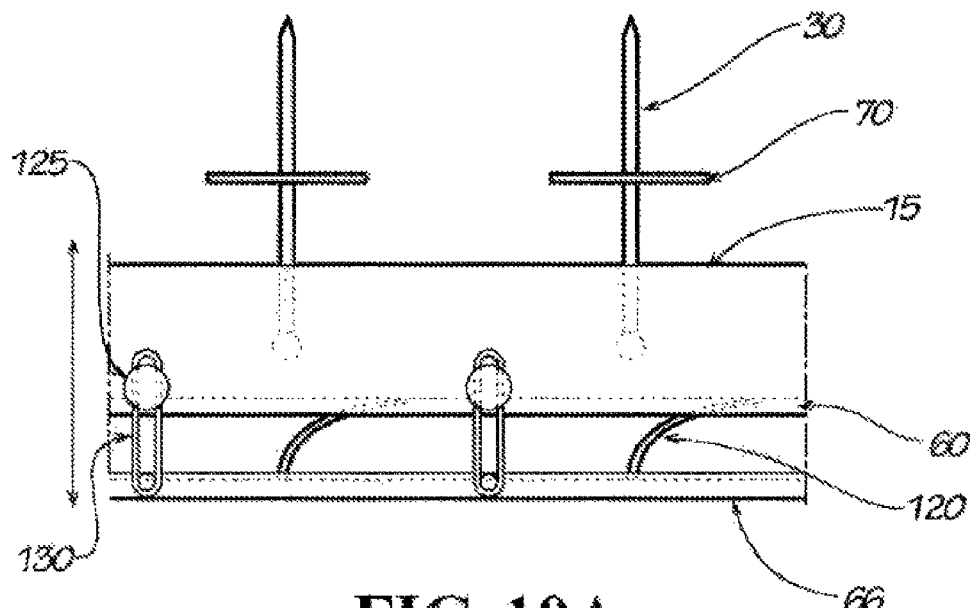
FIGS. 10A and 10B are detailed views of the exemplary embodiment of spring-loaded remodeling attachment members illustrated in FIGS. 9A and 9B according to the present disclosure, in which the band containing attachment members is mounted to a nearly fully extended spring-tensioned suspension.
Figure 10B:
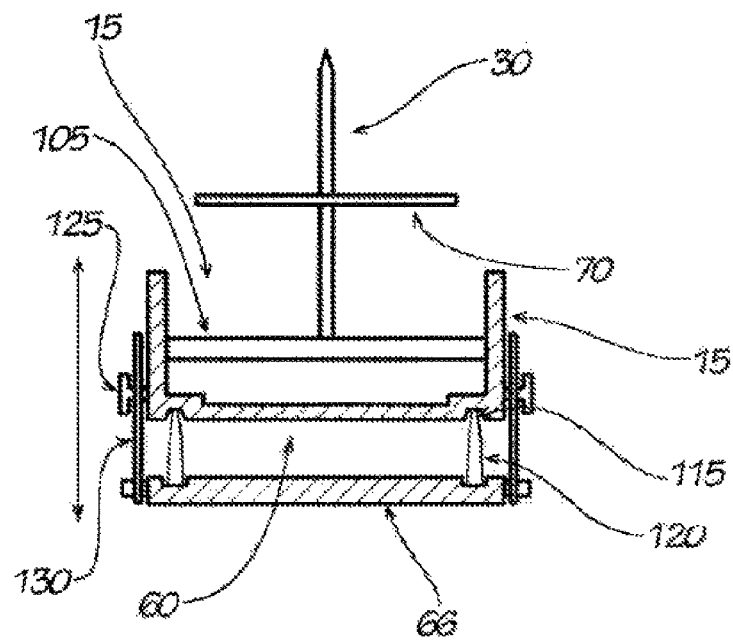

FIGS. 10A and 10B are detailed views of the same exemplary embodiment of spring-loaded remodeling attachment members according to the present disclosure as shown in FIGS. 9A and 9B, but showing the one or more expansion spring elements 120 in a decompressed or fully extended state, with near maximum separation between the sealer belt 60 and sealer belt expansion base 66. Separation between the sealer belt 60 and sealer belt expansion base 66 is limited by the amount of distance allowed by the sliding action of the retention fasteners 125 within the slots of the channel expansion elements 130.

In the exemplary embodiment of spring-loaded remodeling attachment members according to the present disclosure as shown in FIGS. 9A, 9B, 10A, and 10B, any enlargement in the diameter of the recipient anatomic conduit or blood vessel such as post-implantation aortic remodeling would allow the embodiment as shown to automatically accommodate the enlargement and maintain a leak proof seal using the spring tensioned suspension to the limit of the expansion capacity of that suspension.

Figure 11:
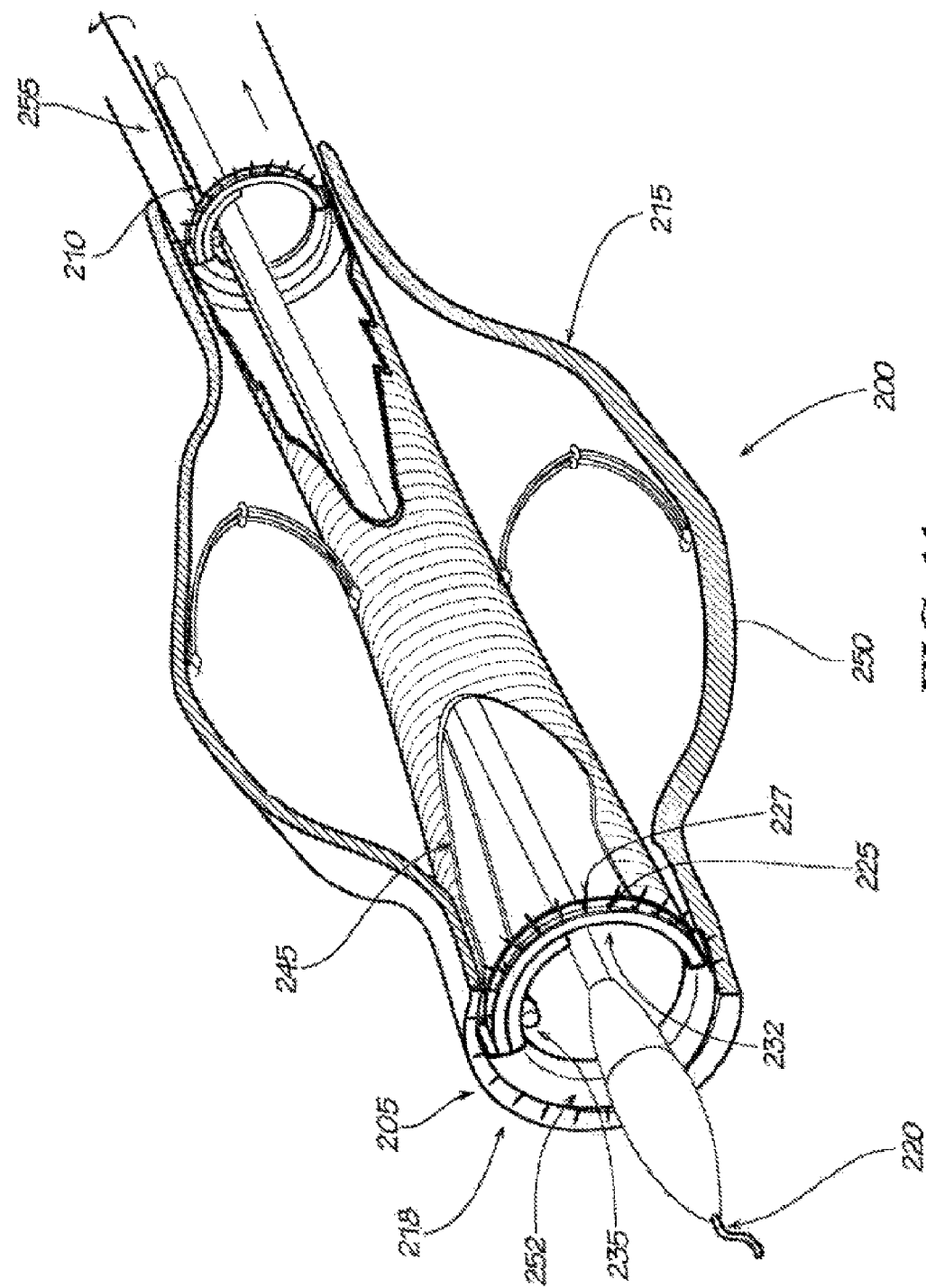
FIG. 11 is a perspective view of an embodiment of an implant interface with circumferential sealable collars and a variable sealing device with a re-docking mechanism according to the present disclosure, with the re-docking mechanism not connected to a removable re-docking control lead.

FIG. 11 is a perspective view of an embodiment of an implant interface with a circumferential sealable collars and a variable sealing device with a re-docking mechanism according to the present disclosure, with the re-docking mechanism not connected to a removable re-docking control lead.

A re-docking mechanism is desirable, should post-implantation changes in the position or size of the implant be desired to either prevent leakages or provide a more advantageous anatomic position.

In FIG. 11, an exemplary endovascular implant graft 200 of this disclosure is shown in an anatomic position within aortic walls 218 and traversing an aneurysm sac 215, said graft comprising a proximal end 205 and a distal end 210. An injection catheter 220 is shown extending through the proximal end 205 of the exemplary endovascular implant graft 200. A tubular corrugated fabric graft 250 is joined proximally by a proximal elastic sealable collar 252. Within the proximal elastic sealable collar 252 are contained a sealer belt 230 provided in an overlapping loop and with a sealer belt channel 225 therewithin, a plurality of retention tines 227 and a compressive foam gasket 240 within the sealer belt channel 225, and a sealing device housing 235. Extending distally within the lumen of the tubular corrugated fabric graft 250 is a re-dockable implant control lead 245.

Figure 12:
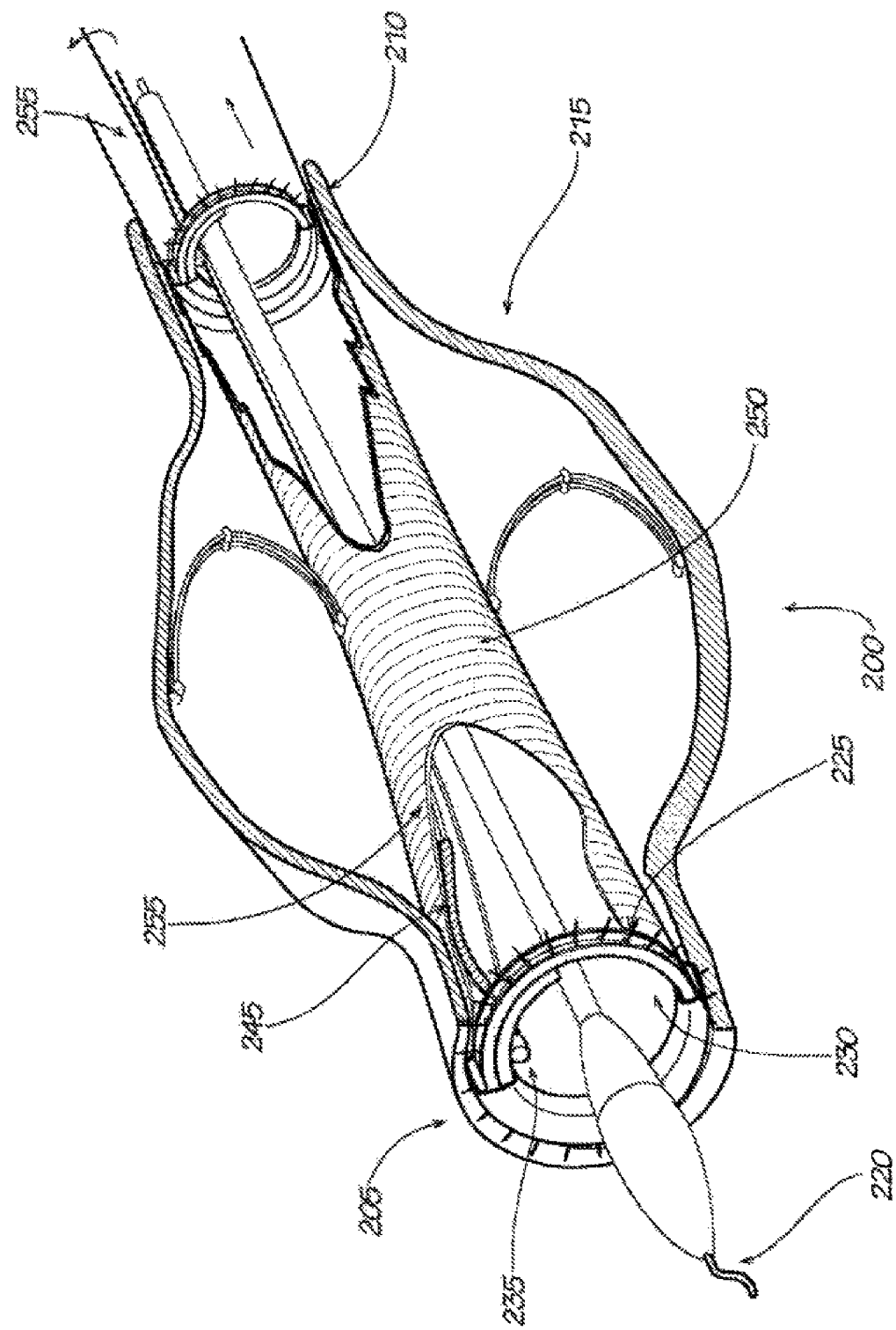
FIG. 12 is a perspective view of an embodiment of an implant interface with a circumferential sealable collars and a variable sealing device with a re-docking mechanism according to the present disclosure, with the re-docking mechanism engaged by a removable re-docking control lead.

FIG. 12 is a perspective view of an embodiment of the same exemplary endovascular implant graft 200 of the present disclosure as shown in FIG. 11, but with a removable re-docking control lead 255 engaged with the re-dockable implant control lead 245. The re-docking control lead 255 as shown in FIG. 12 has been placed into the blood vessel through a distal arteriotomy site (not shown in FIG. 12) by an operator who retains external operative control to allow re-docking and the desired alteration in the configuration and deployment of the endovascular implant graft 200.

Re-docking of the re-dockable implant control lead 245 with a removable re-docking control lead 255 may be achieved by one of several mechanisms according to the present disclosure. The re-dockable implant control lead 245 may be provided with a helix, loop, or distal hook [not shown in the figures herein] that may be snared or otherwise engaged by a guide wire or by the removable re-docking control lead 255. Alternately, magnetic and/or electromagnetic attraction may be employed between the re-dockable implant control lead 245 and the removable re-docking control lead 255 to allow their engagement in a high flow vascular environment. Alternately still, imaging technologies such as intravascular ultrasound and/or optical coherence tomography may be employed to allow an operator using basic endovascular invasive techniques to re-dock and interface with the re-dockable implant control lead 245 post-implantation.

Figure 14:
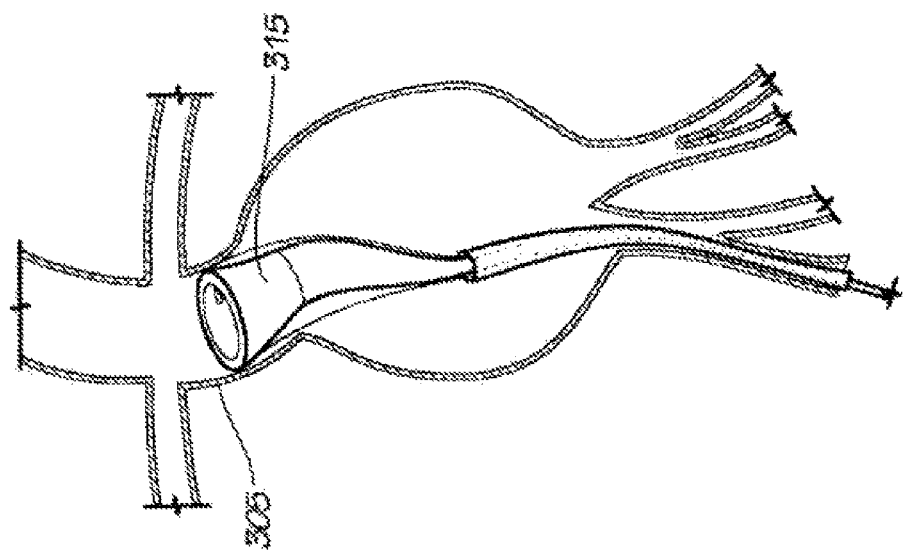
FIG. 14 is a perspective anatomic view of the embodiment of an endograft implant shown in FIG. 13 in which the implant delivery mechanism has been steered to an angular plane of delivery.
Figure 13:
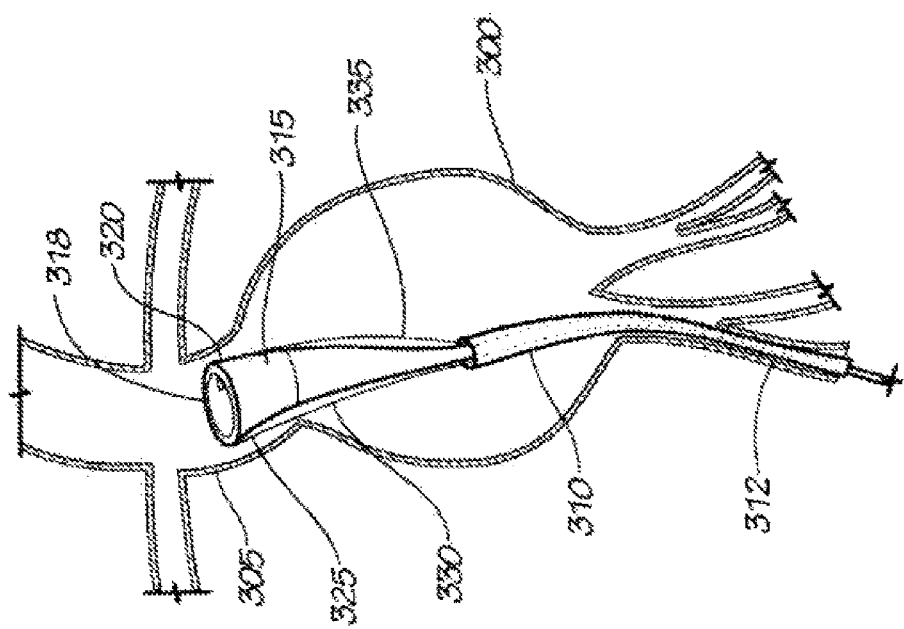
FIG. 13 is a perspective anatomic view of an embodiment of an endograft implant according to the present disclosure in which the implant delivery mechanism is remotely steerable to allow a variable plane of delivery for implantation.
Figure 15:
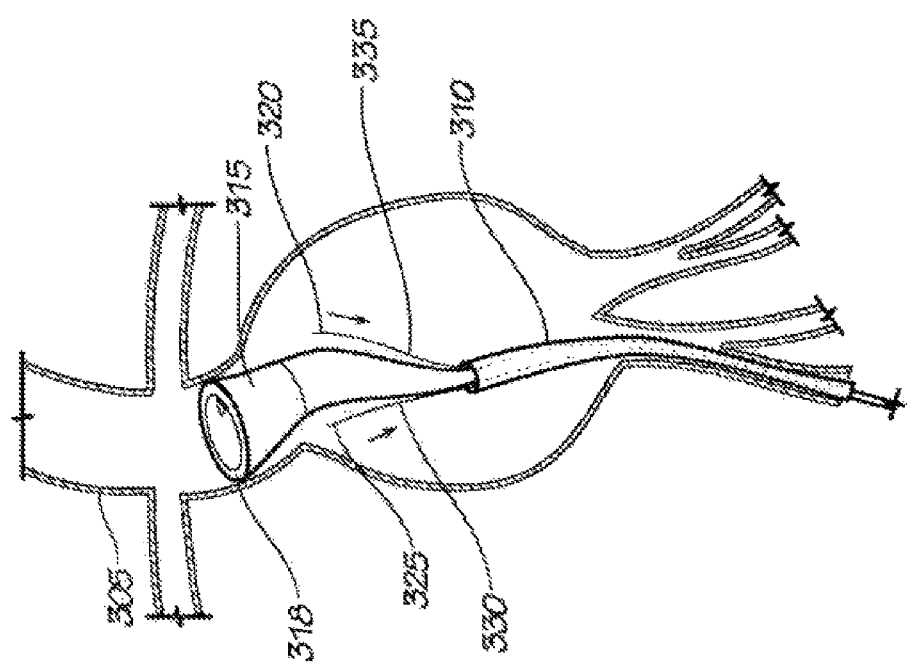
FIG. 15 is a perspective anatomic view of the embodiment of an endograft implant shown in FIG. 14 in which the implant has been sealed and delivered in a desired angular site and the steering mechanism has been disengaged from the implant and is being removed through the delivery catheter.

FIGS. 13-15 show perspective anatomic views of an embodiment of an endograft implant according to the present disclosure in which the implant delivery mechanism is remotely steerable to allow a variable plane of delivery for implantation. The anatomic conditions in the aorta proximal to the desired recipient site for endograft implantation may be irregular or tortuous, ideally requiring an angled deployment of an endograft's proximal interface. Conventional endograft devices do not permit such angled deliveries.

In FIG. 13, an exemplary abdominal aortic aneurysm 300 is shown with a narrow and angled proximal aortic neck 305. A delivery catheter 310 is shown arising from the right iliac artery 312. Extending partially from the delivery catheter 310 is the proximal portion of an exemplary endograft 315 of the present disclosure. As shown in FIG. 13, the endograft 315 comprises a proximal sealable circumferential collar 318 which is connected to a first control wire lead 330 with a removable first control attachment 325 and a second control wire lead 335 with a removable second control attachment 320. Multiple types of attachments are used in various embodiments of the present disclosure to attach the first control wire leads 330 and second control wire leads 335 to the endograft 315. In a preferred embodiment, a removable first control attachment 325 and a removable second control attachment 320 are provided with a coiled tip that may be attached by screw action into the proximal sealable circumferential collar 318. In one aspect and as illustrated in FIGS. 13 and 14, the first control wire lead 330 and the second control wire lead 335 can be of such strength that one control wire lead can be pulled by the operator and the other control wire lead can be pushed by the operator, to achieve the desired angle to accommodate a proper seal.

FIG. 14 shows the endograft implant of FIG. 13 in which the endograft 315 has been steered to a desired angular plane of delivery. Thus, the control wire leads have been used to achieve and maintain a proper proximal seal angle, which is maintained while the gasket is enlarged and the seal is achieved by deploying the times.

FIG. 15 shows the endograft implant of FIG. 14 in which the proximal sealable circumferential collar 318 has been delivered to the desired angular site in the proximal aorta 305 and a seal has been accomplished according to the present disclosure by mechanical alteration of the proximal sealable circumferential collar 318 to seal against and then attach to the aortic wall 305. In FIG. 15, the tines have been deployed, and the removable first control attachment 325 and the removable second control attachment 320 are shown disengaged from the proximal sealable circumferential collar 318. Also in FIG. 15, the first control wire lead 330, the removable first control attachment 325, the second control wire lead 335, and the removable second control attachment 320 are shown being removed through the delivery catheter 310.

Figure 16:
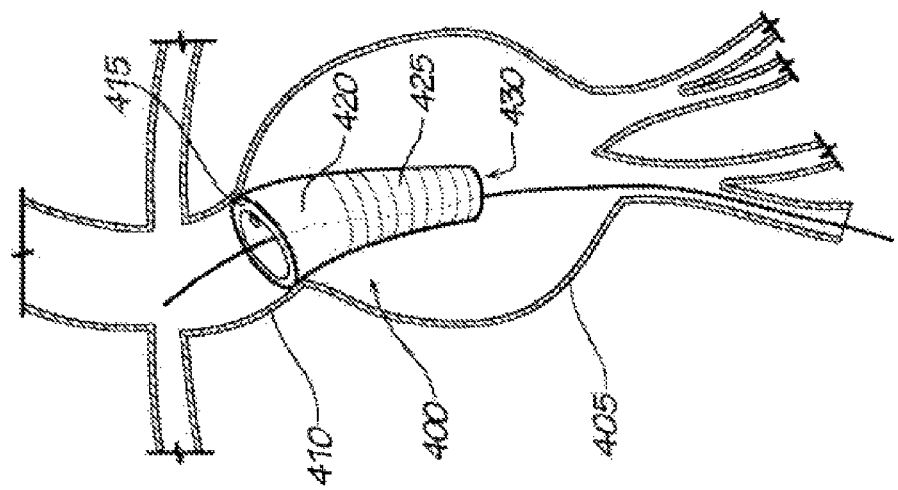
FIG. 16 shows a perspective anatomic view of an exemplary embodiment of an endograft implant according to the present disclosure in which the implant is a universal proximal cuff implant for treatment of an abdominal aortic aneurysm.

FIG. 16 shows a perspective anatomic view of an exemplary embodiment of an endograft implant according to this disclosure in which the implant is a universal proximal cuff endovascular implant for treatment of an abdominal aortic aneurysm. Endografts with the features shown in the various embodiments of the present disclosure have unique abilities to accommodate to anatomic variations that would preclude or compromise use of conventional endograft systems. For example, non-conducive anatomy can arise by virtue of angulation, calcific disease, thrombus, or a short neck. The universal proximal cuff implants of the present disclosure allow an operator to make use of their ability to securely seal and attach in anatomic sites where conventional endografts cannot be securely placed, and then allow a conventional endograft to securely dock with the universal proximal cuff endovascular implants distally.

In FIG. 16, a universal proximal cuff endovascular implant 400 has been placed in a narrow and angulated proximal aortic neck 410 and extends into an abdominal aortic aneurysm 405. The universal proximal cuff endovascular implant 400 comprises a proximal sealable circumferential collar 415 of the present disclosure, which is connected to an elastic proximal end 420 of a non-elastic tubular implant body 425 with a distal docking opening 430. The device of FIG. 16 has been delivered and implanted with the techniques of this disclosure, and contains a variable sealing device and attachment retention tines of this disclosure (not shown in FIG. 16). Once the device of FIG. 16 has been implanted as shown, an operator may engage and deliver any endograft including conventional endografts to the distal docking opening 430. Thus, the universal proximal cuff endovascular implant 400 provides a conduit that is suspended into, or extends into, the into an abdominal aortic aneurysm 405, that can serve as a neck conducive for docking any known endograft.

Figure 17:
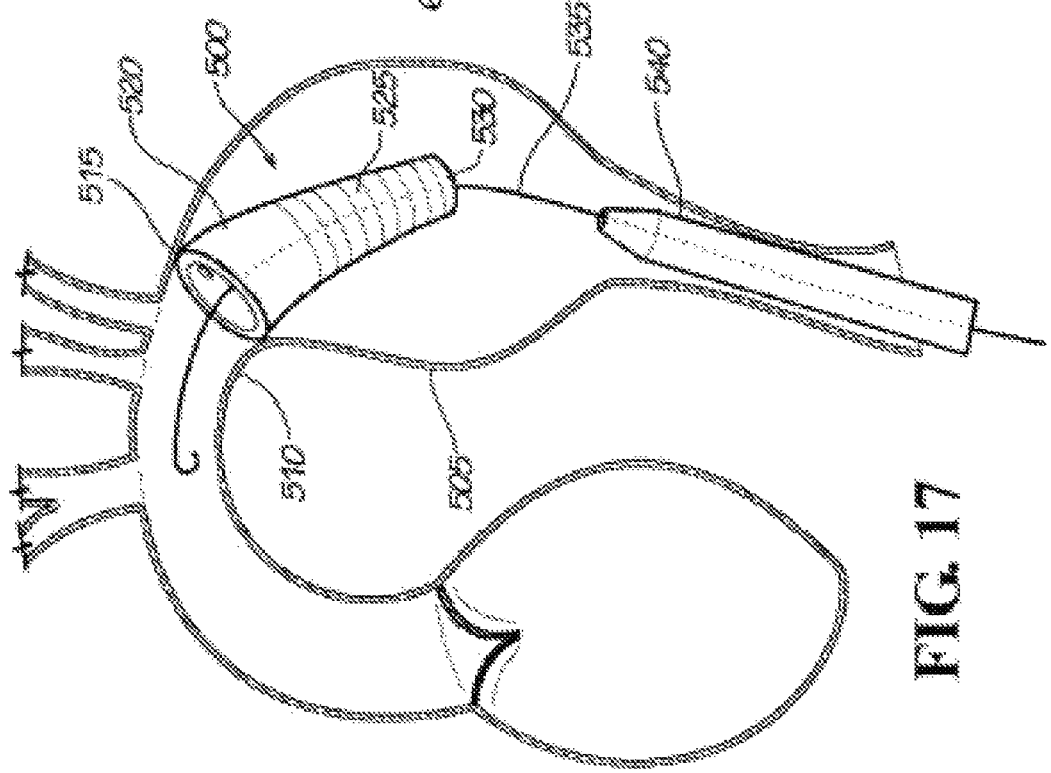
FIG. 17 shows a perspective anatomic view of an exemplary embodiment of an endograft implant according to the present disclosure in which the implant is a universal proximal cuff implant for treatment of a thoracic aortic aneurysm.

FIG. 17 shows a perspective anatomic view of an exemplary embodiment of an endograft implant according to the present disclosure in which the implant is a universal proximal cuff endovascular implant for treatment of a thoracic aortic aneurysm.

In FIG. 17, a universal proximal cuff endovascular implant 500 has been placed in a narrow and angulated proximal aortic neck 510 and extends into a descending thoracic aortic aneurysm 505. The universal proximal cuff endovascular implant 500 comprises a proximal sealable circumferential collar 515 of the present disclosure, which is connected to an elastic proximal end 520 of a non-elastic tubular implant body 525 with a distal docking opening 530. The device of FIG. 17 has been delivered and implanted with the techniques of the present disclosure, and contains a variable sealing device and attachment retention tines of the present disclosure (not shown in FIG. 16). Once the device of FIG. 17 has been implanted as shown, an operator may engage and deliver any endograft including conventional endografts to the distal docking opening 530. FIG. 17 shows such a delivery in progress, with a guide wire 535 in place, and a delivery catheter 540 containing an endograft being introduced for delivery into the distal docking opening 530.

Figure 18:
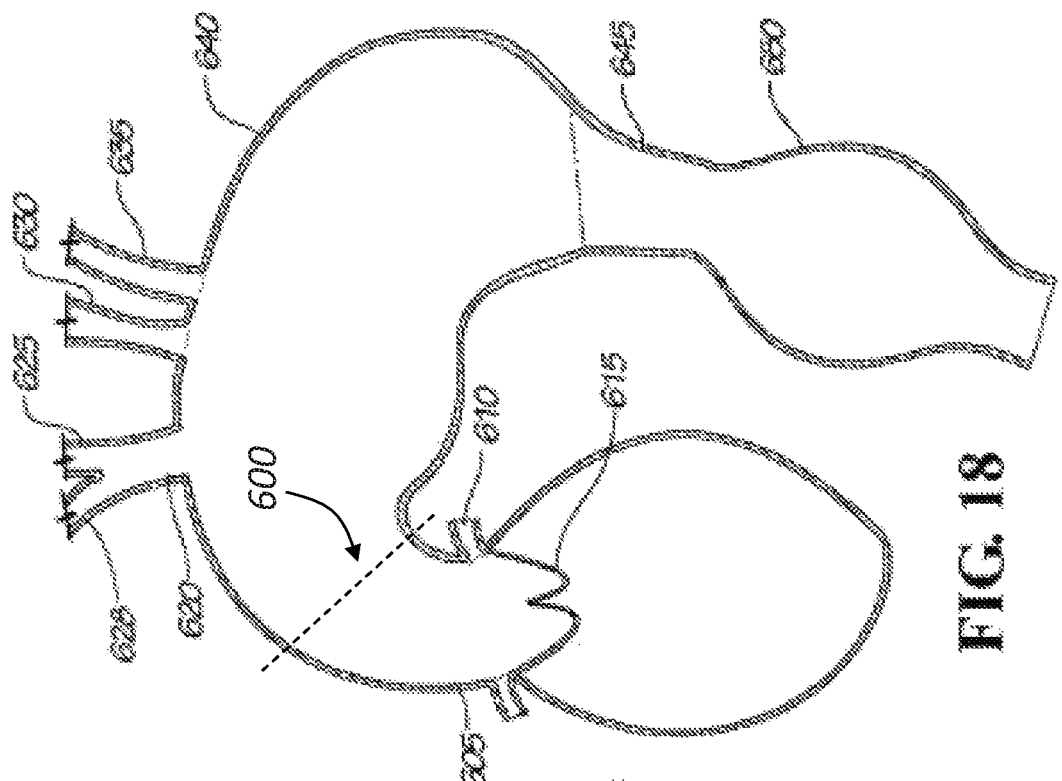
FIG. 18 is an anatomic drawing which shows a complex aortic arch with a first aneurysm involving the aortic arch and a second aneurysm involving the descending aorta.
Figure 20:
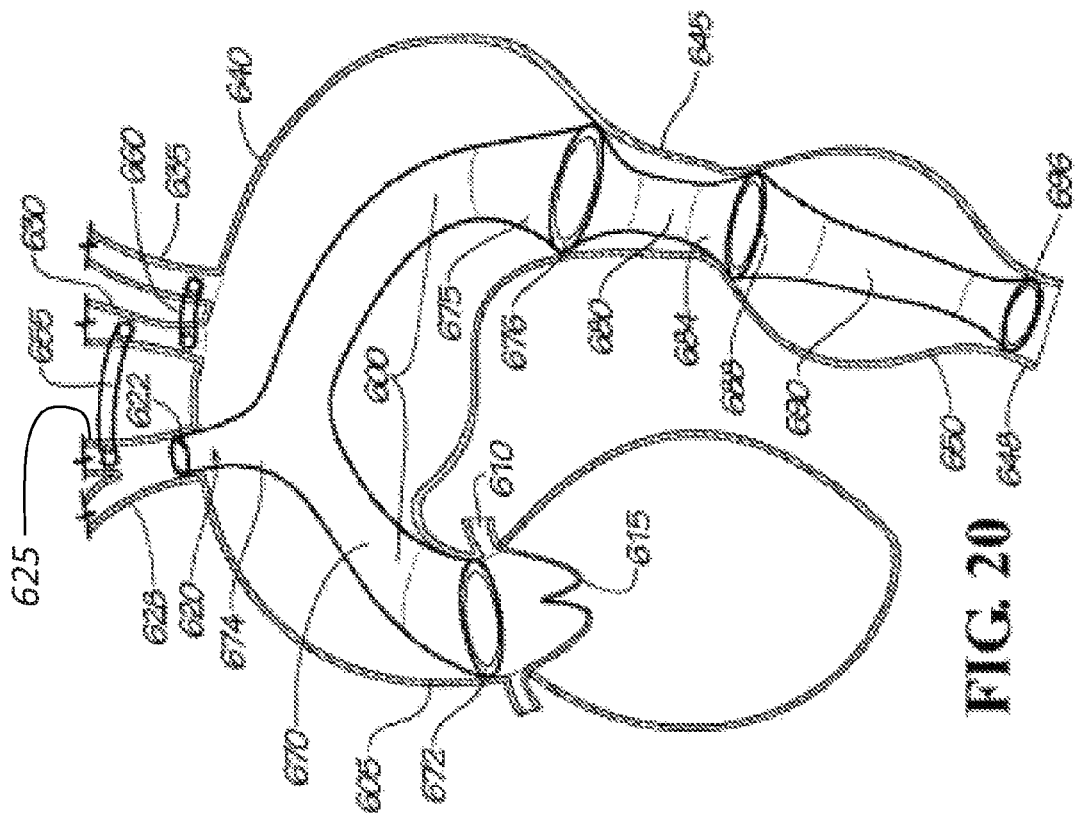
FIG. 20 shows the same view as FIG. 19, with exemplary endovascular placement of three embodiments of endografts of the present disclosure to traverse the pathology and maintain vital circulation.
Figure 19:
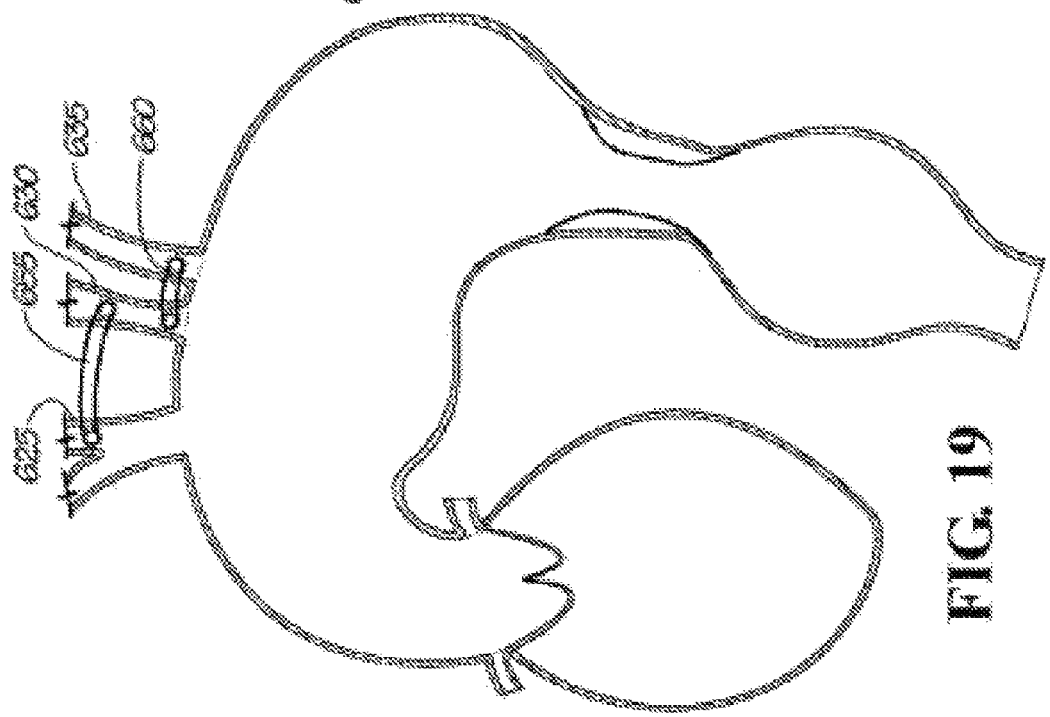
FIG. 19 shows the anatomic situation of FIG. 18, in which extra-anatomic surgical bypass has been performed with bypasses between the right and left carotid and between the left carotid and left subclavian arteries.

FIGS. 18-20 show an exemplary pathologic condition with a complex aortic arch with a first aneurysm involving the aortic arch and a second aneurysm involving the descending aorta. Such a condition would not be treatable with conventional endografts. In FIG. 18, the ascending aorta 605 arises above the aortic valve 615 and gives off the coronary arteries 610. The area between the ascending aorta 605 and the descending thoracic aorta 645 is the aortic arch 600. The aortic arch 600 gives rise to the innominate artery 620 which divides into the right subclavian artery 628 and right common carotid artery 625, The aortic arch 600 further gives rise to the left common carotid artery 630 and the left subclavian artery 635. The right subclavian artery 628, right common carotid artery 625, left common carotid artery 630 and the left subclavian artery 635 are critical blood vessels to supply arterial blood to the arms, head, neck, and brain. FIG. 18 further shows a large first aneurysm 640 involving the aortic arch 600 and a second aneurysm 650 involving the descending thoracic aorta 645.

FIG. 19 shows the anatomic situation of FIG. 18, in which extra-anatomic surgical bypass has been performed with a first bypass 655 between the right common carotid artery 625 and left common carotid artery 630 and a second bypass 660 between the left common carotid artery 630 and the left subclavian artery 635.

FIG. 20 shows the same view as FIG. 19, with exemplary endovascular placement of three embodiments of endografts of the present disclosure to traverse the pathology and maintain vital circulation.

In FIG. 20, a first endograft 670 of the present disclosure has been placed through the aortic arch 600 with an attachment in the ascending aorta just distal to the coronary arteries using a first proximal sealable circumferential collar 672 of the present disclosure. The first endograft 670 as shown has an innominate branch 620 with an innominate sealable circumferential collar 622. The first endograft 670 traverses and excludes the first aneurysm 640 and terminates in a distal cuff 675 at the distal end of the aortic arch 600. A second endograft 680 connects to the distal cuff 675 of the first endograft 670 using a second proximal sealable circumferential collar 676 of the present disclosure's design.

As shown in FIG. 20, the second endograft 680 traverses a segment of the descending aorta 645. The second endograft 680 may be fenestrated [not shown in FIG. 20] either in manufacture or surgically to allow collateral circulation to be maintained to the spinal and other vessels arising from that segment of the descending aorta 645.

FIG. 20 further shows a second aneurysm 650 in the descending aorta 645. In FIG. 20, this is traversed and excluded by a third endograft 690 of the present disclosure, which is shown sealably attaching to the second endograft distal cuff 684 with a third proximal sealable circumferential collar 688 of the present disclosure's design. The third endograft 690 is shown attaching distally with a distal sealable circumferential collar 696 of the present disclosure's design.

Thus, in FIG. 20, circulation is maintained to the arms, head, brain, and spine, while excluding two difficult thoracic aneurysms. This exemplary combination of endografts of the present disclosure and a relatively minor vascular procedure allows complete treatment of very difficult anatomic pathology that would be beyond the reach of conventional endovascular techniques and devices. This makes a variety of aortic arch pathologies within the scope of the devices and methods of this disclosure, including aortic arch aneurysms, dissecting aneurysms of the aortic arch, transposition of the great vessels, and other complex pathologies.

In addition to the making and use of endovascular implant grafts, other anatomic applications are also within the scope of the present disclosure. As an example, the mechanisms and principles disclosed herein may be applied to gastrointestinal disorders, where an intralumenal bypass may be desirable that may be placed using endoscopic techniques.

Crohn's disease (also known as regional) is a chronic, episodic, inflammatory bowel disease (IBD) and is generally classified as an autoimmune disease. Crohn's disease can affect any part of the gastrointestinal tract from mouth to anus; as a result, the symptoms of Crohn's disease vary among afflicted individuals. The disease is characterized by areas of inflammation with areas of normal lining between in a symptom known as skip lesions. The main gastrointestinal symptoms are abdominal pain, diarrhea (which may be bloody, though this may not be visible to the naked eye), constipation, vomiting, weight loss or weight gain. Crohn's disease typically involves the terminal ileum.

In an exemplary embodiment of a gastrointestinal aspect of the present disclosure, a tubular graft comprising proximal and distal sealable implant interfaces as disclosed herein is endoscopically placed and affixed proximally to and distally to a segment of intestine affected by Crohn's disease to divert the intestinal contents therethrough.

By providing an intraintestinal bypass for the conduit of intestinal contents though areas affected by Crohn's disease, local inflammatory response and sequelae in the affected areas are reduced.

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. Therefore, the description and examples presented herein should not be construed to limit the scope of the present disclosure.

Co-pending U.S. patent application Ser. No. 11/888,009, filed Jul. 31, 2007, is incorporated by reference herein in its entirety. Any other publications and patents mentioned in this disclosure are incorporated herein by reference in their entireties, for the purpose of describing and disclosing the constructs and methodologies described in those publications and patents, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that may be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

We claim:

1. An endograft implant system, comprising:
an implant delivery catheter sized to be placed within an anatomic space comprising an internal wall, the implant delivery catheter comprising:
a sheath defining a lumen;
an external end; and
an internal end; and
an endograft implant at least one of compressed and folded within the lumen at the internal end of the implant delivery catheter lumen, the endograft implant comprising:
a tubular implant body comprising an elastic end and an implant lumen, the elastic end comprising a sealable circumferential collar having a diameter;
a variable sealing device contained within the sealable circumferential collar, the variable sealing device being operable to reversibly vary the diameter of the sealable circumferential collar;
a control lead releasably, directly, and mechanically connected to the variable sealing device to reversibly vary the diameter of the variable sealing device when the control lead is rotated; and
a plurality of retractable retention tines pivotally mounted within the variable sealing device such that, when the control lead is rotated to expand the diameter of the sealable circumferential collar, the retractable retention tines are exposed outwardly from the variable sealing device to engage the internal wall adjacent the elastic end and, when the control lead is rotated to reduce the diameter of the sealable circumferential collar, the retractable retention tines withdraw inwardly into the variable sealing device.

2. The endograft implant system according to claim 1, wherein the implant delivery catheter and the sheath each have a length that allows advancement of the implant delivery catheter and the sheath into at least one of the thoracic aorta and the abdominal aorta.

3. The endograft implant system according to claim 1, wherein the control lead traverses the implant delivery catheter and exits at the external end of the implant delivery catheter.

4. The endograft implant system according to claim 1, wherein the variable sealing device comprises:
   a sealer belt provided in an overlapping loop comprising a sealer belt channel, sealer gear retainment slots within the sealer belt channel, and two sealer belt channel side walls, the plurality of retention tines being pivotally mounted within the sealer belt channel, the retention tines within the outermost sealer belt channel circumference being disposed outwardly to engage an anatomic lumenal wall;
   a compressible foam gasket contained within the sealer belt channel and situated between the sealer belt and an outermost circumference of the sealable circumferential collar;
   a sealing device housing comprising a sealer gear having an axis parallel with the axis of the sealer belt and being rotatably mounted within the sealing device housing to interface with the sealer gear retainment slots; and
   a spring interface within the sealer gear releasably connected to the control lead such that axial compression of the spring interface with the control lead unlocks a locking member and allows rotation of the sealer gear to reversibly vary the diameter of the variable sealing device.

5. The endograft implant system according to claim 4, wherein the sealer belt is of at least one of titanium, stainless steel, a cobalt chromium alloy, a metal, a metal alloy, a polymer, a plastic, and a ceramic.

6. The endograft implant system according to claim 1, wherein the sealable circumferential collar comprises an expandable mesh.

7. The endograft implant system according to claim 1, wherein the sealable circumferential collar comprises one of:
   a self-expandable mesh endoskeleton; and
   a self-expandable mesh exoskeleton capable of self-expanding such that longitudinal traction on the expanded mesh reduces the circumference of the sealable circumferential collar.

8. The endograft implant system according to claim 1, wherein the endograft implant comprises a biocompatible material or is coated with a biocompatible material.

9. The endograft implant system according to claim 8, wherein the biocompatible material is a polymer comprising fluorinated monomer units selected from at least one of —CF2CF2-, —CH2CF2-, —CH2CHF—, —CHFCHF—, —CClFCF2-, —CF2C(CF3)F—, —CHFC(CF3)F—, —CF2C(CF3)H—, —CF2CRF—, —CHFCRF—, —CF2CRH—, —CH2CRF—, and —CFHCRH—, wherein R in each occurrence is selected independently from H, Cl, Br, I, methyl, ethyl, n-propyl, isopropyl, short chain alkyl groups, phenyl, substituted phenyl, cyclic alkyl, heterocyclic, heteroaryl, fluorinated short chain alkyl groups, fluorinated phenyl, fluorinated cyclic alkyl, fluorinated heterocyclic, or combinations thereof.

10. The endograft implant system according to claim 8, wherein the endograft implant comprises a biocompatible material or is coated with a biocompatible material selected from at least one of poly(ethylene glycol) (PEG), polypropylene, poly(propylene glycol) (PPG), poly(N-vinyl pyrrolidone) (PVP), poly(N-vinyl pyrrolidone-co-vinyl acetate) (Copovidone), poly(ester amides) (PEA), acrylic acid (AA), polyacrylates, acrylamides, fluorinated polymers or copolymers, poly(hydroxyvalerate), poly(L-lactic acid)/polylactide (PLLA), poly(E-caprolactone), poly(lactide-co-glycolide) (PLGA), poly(hydroxybutyrate), poly(hydroxyvalerate), poly(hydroxybutyrate-co-valerate), polydioxanone, poly-orthoesters, polyanhydrides, poly(glycolic acid)/polyglycolide (PGA), poly(D,L-lactic acid) (PLA), poly(glycolic acid-co-trimethylene carbonate), polyphosphoesters, polyurethanes, polyureas, polyurethane(ureas), poly(amino acids), cyanoacrylates, poly(trimethylene carbonate), poly(iminocarbonates), co-poly(etheresters), polyalkylene oxalates, polyphosphazenes, silicones, polyesters, polyolefins, polyisobutylene and ethylene-.alpha.-olefin copolymers, vinyl halide polymers and copolymers, polyvinyl ethers, polyvinylidene chloride, polyacrylonitrile, polyvinyl ketones, polyvinyl aromatics, polyvinyl esters, copolymers of vinyl monomers with each other, olefins, poly(vinyl alcohol) (PVA), acrylonitrile butadiene (ABS) resins, ethylene-vinyl acetate copolymers, polyamides, alkyl resins, polycarbonates, polyoxymethylenes, polyimides, polyethers, epoxy resins, rayon, rayon-triacetate, and combinations and co-polymers thereof.

11. The endograft implant system according to claim 1, wherein the tubular implant body is nonelastic.

12. The endograft implant system according to claim 1, wherein the sealable circumferential collar is elastic.

13. The endograft implant system according to claim 1, wherein the tubular body as fabricated is substantially non-linear.

14. The endograft implant system according to claim 1, wherein the tubular body is branched.

15. The endograft implant system according to claim 1, wherein the variable sealing device has a diameter adjusted to achieve a substantially fluid-tight seal between the sealable circumferential collar and the internal wall of the anatomic space in which it is located.

16. The endograft implant system according to claim 1, wherein the endograft implant is a first endograft implant and is connected in series with one or more additional endograft implants to achieve a substantially fluid-tight seal between the first endograft implant and any additional endograft implant.

17. The endograft implant system according to claim 16, wherein the first endograft implant and at least one additional endograft implant are connected in series so as to substantially exclude areas of normal lumen therebetween and to achieve a substantially fluid-tight seal between the first endograft implant and the at least one additional endograft implant.

18. The endograft implant system according to claim 1, wherein:
   the elastic end of the tubular implant body is an elastic proximal end and the sealable circumferential collar is a proximal sealable circumferential collar;
   the variable sealing device is at the elastic proximal end and is operable to reversibly vary the diameter of the proximal sealable circumferential collar;
   the control lead is a proximal control lead releasably, directly, and mechanically connected to the variable sealing device to reversibly vary the diameter of the variable sealing device at the elastic proximal end when the control lead is rotated; and
   the plurality of retractable retention tines are pivotally mounted within the variable sealing device such that, when the proximal control lead is rotated to expand the diameter of the proximal sealable circumferential collar, the retractable retention tines are exposed outwardly from the variable sealing device to engage the internal wall adjacent the elastic proximal end and, when the control lead is rotated to reduce the diameter of the proximal sealable circumferential collar, the retractable retention tines withdraw inwardly into the variable sealing device.

19. The endograft implant system according to claim 1, wherein:
the elastic end of the tubular implant body is an elastic distal end and the sealable circumferential collar is a distal sealable circumferential collar;
the variable sealing device is at the elastic distal end and is operable to reversibly vary the diameter of the distal sealable circumferential collar;
the control lead is a distal control lead releasably, directly, and mechanically connected to the variable sealing device to reversibly vary the diameter of the variable sealing device at the elastic distal end when the control lead is rotated; and
the plurality of retractable retention tines are pivotally mounted within the variable sealing device such that, when the distal control lead is rotated to expand the diameter of the distal sealable circumferential collar, the retractable retention tines are exposed outwardly from the variable sealing device to engage the internal wall adjacent the elastic distal end and, when the control lead is rotated to reduce the diameter of the distal sealable circumferential collar, the retractable retention tines withdraw inwardly into the variable sealing device.

20. The endograft implant system according to claim 1, wherein:
the tubular implant body comprises a proximal elastic end and a distal elastic end;
the sealable circumferential collar is a pair of proximal and distal sealable circumferential collars respectively at the proximal and distal elastic ends and respectively having a proximal variable sealing device and a distal variable sealing device;
the proximal variable sealing device is at the proximal elastic end and is operable to reversibly vary the diameter of the proximal sealable circumferential collar;
the distal variable sealing device is at the distal elastic end and is operable to reversibly vary the diameter of the distal sealable circumferential collar;
the control lead is a pair of proximal and distal control leads;
the proximal control lead is releasably, directly, and mechanically connected to the proximal variable sealing device to reversibly vary the diameter of the proximal variable sealing device at the elastic proximal end when the proximal control lead is rotated; and
the distal control lead is releasably, directly, and mechanically connected to the distal variable sealing device to reversibly vary the diameter of the distal variable sealing device at the elastic distal end when the distal control lead is rotated.

* * * * *